(12) United States Patent
Sano et al.

(10) Patent No.: US 12,186,075 B2
(45) Date of Patent: *Jan. 7, 2025

(54) ABNORMAL DATA PROCESSING SYSTEM AND ABNORMAL DATA PROCESSING METHOD

(71) Applicant: Maxell, Ltd., Kyoto (JP)

(72) Inventors: Yuko Sano, Tokyo (JP); Akihiko Kandori, Tokyo (JP); Tomohiko Mizuguchi, Oyamazaki (JP); Ying Yin, Beijing (CN)

(73) Assignee: MAXELL, LTD., Kyoto (JP)

( * ) Notice: Subject to any disclaimer, the term of this patent is extended or adjusted under 35 U.S.C. 154(b) by 25 days.

This patent is subject to a terminal disclaimer.

(21) Appl. No.: 18/095,719

(22) Filed: Jan. 11, 2023

(65) Prior Publication Data

US 2023/0165487 A1 Jun. 1, 2023

Related U.S. Application Data

(63) Continuation of application No. 16/756,170, filed as application No. PCT/JP2018/038709 on Oct. 17, 2018, now Pat. No. 11,607,153.

(30) Foreign Application Priority Data

Oct. 30, 2017 (JP) .................. 2017-209127

(51) Int. Cl.
*A61B 5/11* (2006.01)
*G06F 3/04883* (2022.01)

(52) U.S. Cl.
CPC ........... *A61B 5/1124* (2013.01); *A61B 5/1114* (2013.01); *A61B 5/1122* (2013.01); *G06F 3/04883* (2013.01)

(58) Field of Classification Search
None
See application file for complete search history.

(56) References Cited

U.S. PATENT DOCUMENTS

2005/0215868 A1 9/2005 Kenjou et al.
2007/0177771 A1 8/2007 Tanaka et al.
(Continued)

FOREIGN PATENT DOCUMENTS

JP 2000-166881 A 6/2000
JP 2003-204942 A 7/2003
(Continued)

OTHER PUBLICATIONS

International Search Report of PCT/JP2018/038709 dated Jan. 15, 2019.
(Continued)

*Primary Examiner* — Kirk W Hermann
(74) *Attorney, Agent, or Firm* — MATTINGLY & MALUR, PC

(57) ABSTRACT

The abnormal data processing system is provided with: a storage unit for holding a multiple-subject DB in which data on multiple subjects are accumulated and individual-subject DB in which data on individual subjects are accumulated; an individual-subject DB divergence-degree calculation unit for calculating an individual-subject DB divergence degree which is the degree of divergence of the new data from the individual-subject DB; a multiple-subject DB divergence degree calculation unit for calculating a multiple-subject DB divergence degree which is the degree of divergence of the new data from the multiple-subject DB; and a composite divergence degree calculation unit for determining a composite divergence by compositing the individual-subject DB divergence degree and the multiple-subject DB divergence degree using the number of data instances in the individual-subject DB. The abnormal data processing system deter-
(Continued)

mines whether or not the new data is abnormal on the basis of the composite divergence degree.

9 Claims, 27 Drawing Sheets

(56) References Cited

U.S. PATENT DOCUMENTS

| | | | |
|---|---|---|---|
| 2010/0106060 A1* | 4/2010 | Tsuji | A61B 5/1101 600/587 |
| 2011/0201902 A1 | 8/2011 | Shiga et al. | |
| 2013/0044927 A1 | 2/2013 | Poole | |
| 2013/0304710 A1 | 11/2013 | Nachev | |
| 2015/0193588 A1 | 7/2015 | Nemoto et al. | |
| 2016/0100788 A1* | 4/2016 | Sano | A61B 5/4094 600/595 |
| 2019/0005433 A1* | 1/2019 | Sekine | G05B 23/0235 |

FOREIGN PATENT DOCUMENTS

| | | | | |
|---|---|---|---|---|
| JP | 2005152053 A | * | 6/2005 | |
| JP | 2005-305134 A | | 11/2005 | |
| JP | 2007-202869 A | | 8/2007 | |
| JP | 2010-122901 A | | 6/2010 | |
| JP | 2011-238215 A | | 11/2011 | |
| JP | 2013-039344 A | | 2/2013 | |
| JP | 2013-535268 A | | 9/2013 | |
| JP | 2017-140424 A | | 8/2017 | |
| JP | 2017-189444 A | | 10/2017 | |
| JP | 2018-156639 A | | 10/2018 | |
| KR | 1855286 B1 | * | 5/2018 | ........... A61B 5/0022 |
| WO | 2015/050174 A1 | | 4/2015 | |
| WO | WO-2016031348 A1 | * | 3/2016 | ........... A61B 5/0022 |

OTHER PUBLICATIONS

Japanese Office Action received in corresponding Japanese Application No. 2022-023708 dated Jan. 17, 2023.

* cited by examiner

F I G. 6
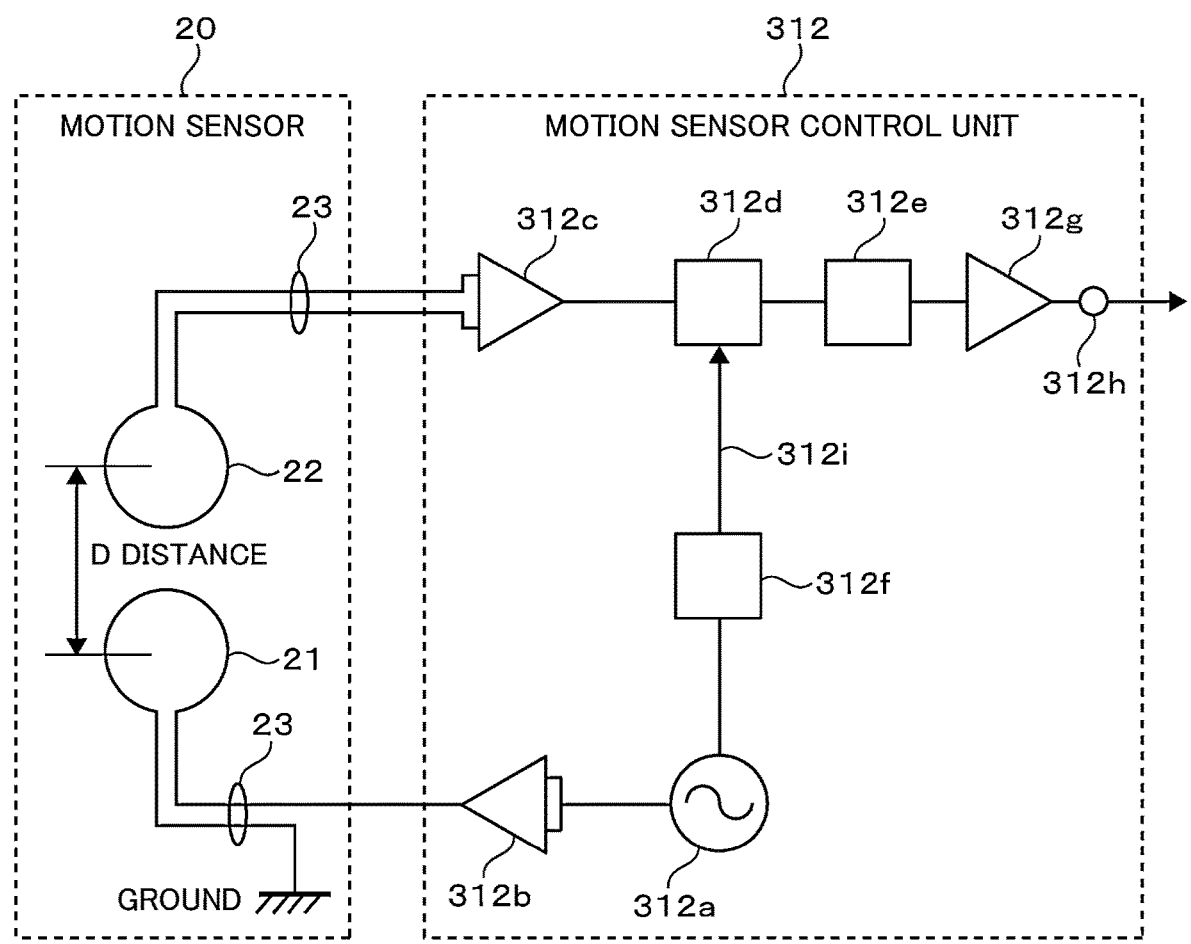

F I G. 9

FEATURE AMOUNT LIST 50A

| FEATURE AMOUNT CLASSIFICATION | IDENTIFICATION NUMBER | FEATURE AMOUNT PARAMETER [UNIT] |
|---|---|---|
| DISTANCE | 1 | MAXIMUM AMPLITUDE OF DISTANCE [mm] |
| | 2 | TOTAL MOVEMENT DISTANCE [mm] |
| | 3 | AVERAGE OF LOCAL MAXIMUM POINTS OF DISTANCE [mm] |
| | 4 | STANDARD DEVIATION OF LOCAL MAXIMUM POINT OF DISTANCE [mm] |
| | 5 | SLOPE (ATTENUATION RATE) OF APPROXIMATE STRAIGHT LINE OF LOCAL MAXIMUM POINT OF DISTANCE [mm/sec] |
| | 6 | VARIATION COEFFICIENT OF LOCAL MAXIMUM POINT OF DISTANCE [–] |
| | 7 | STANDARD DEVIATION OF LOCAL MAXIMUM POINT OF DISTANCE [mm] |
| ... | ... | ... |

F I G. 1 0
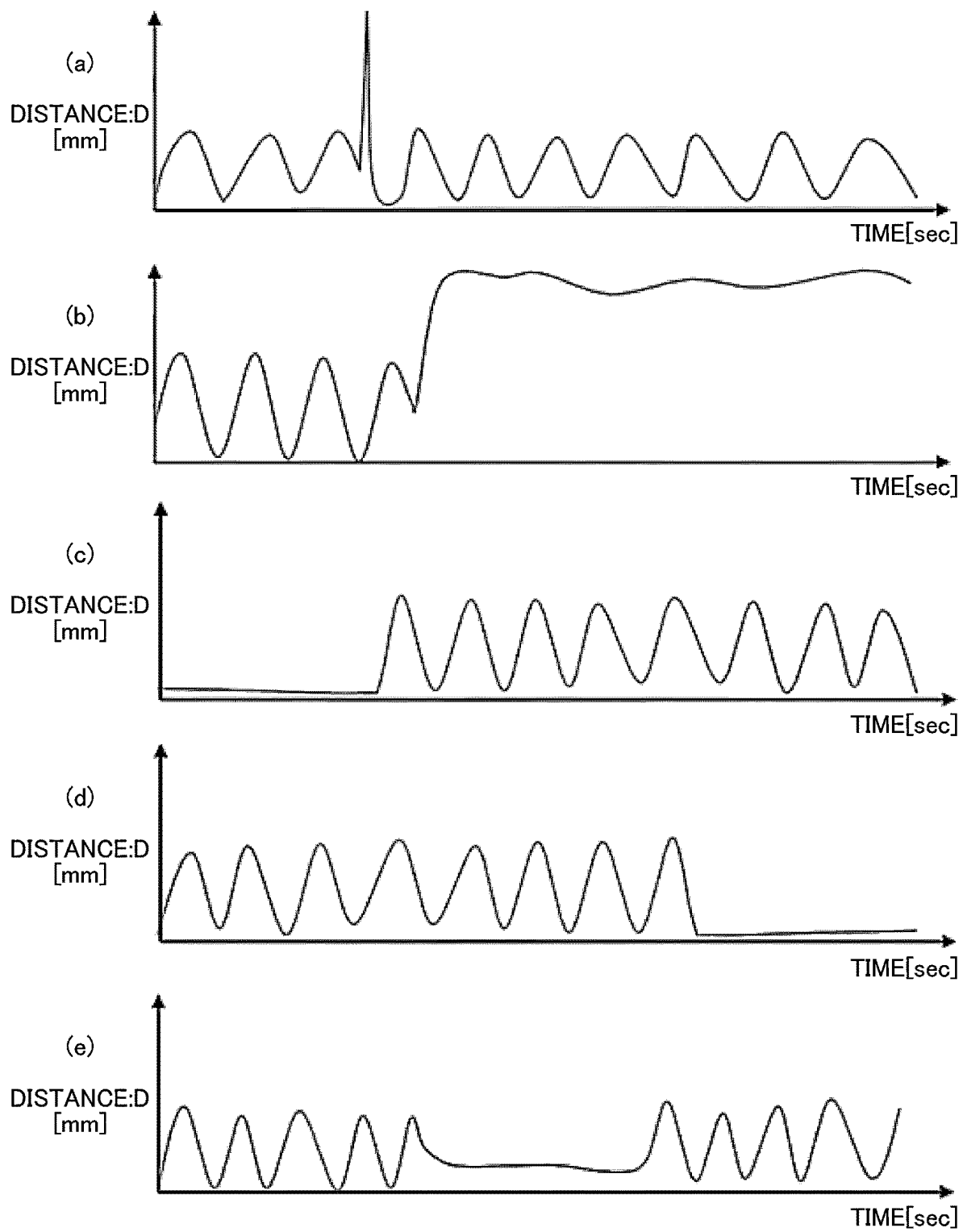

FIG. 12
CALCULATION OF COMPOSITE DEGREE OF DIVERGENCE
(a)
MULTIPLE-SUBJECT DB
DIVERGENCE DEGREE d2
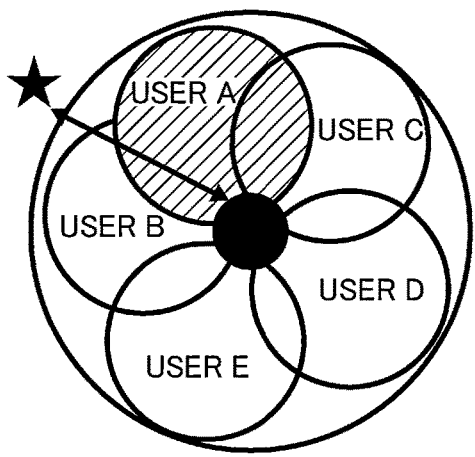
INDIVIDUAL-SUBJECT DB
DIVERGENCE DEGREE d1
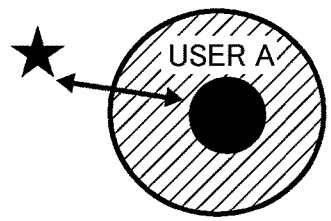
$\times (1-c)$ $\times c$
COMPOSITE DEGREE OF DIVERGENCE ds
(b)
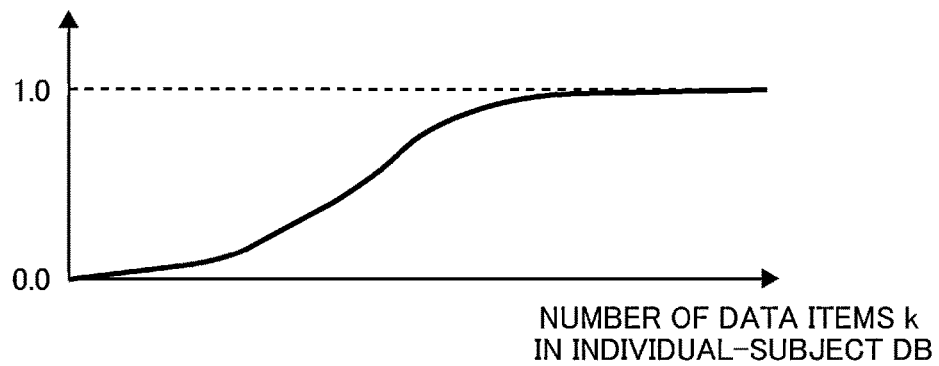

FIG. 13
CALCULATION OF TEMPORAL ATTENUATION DIVERGENCE DEGREE
(a)
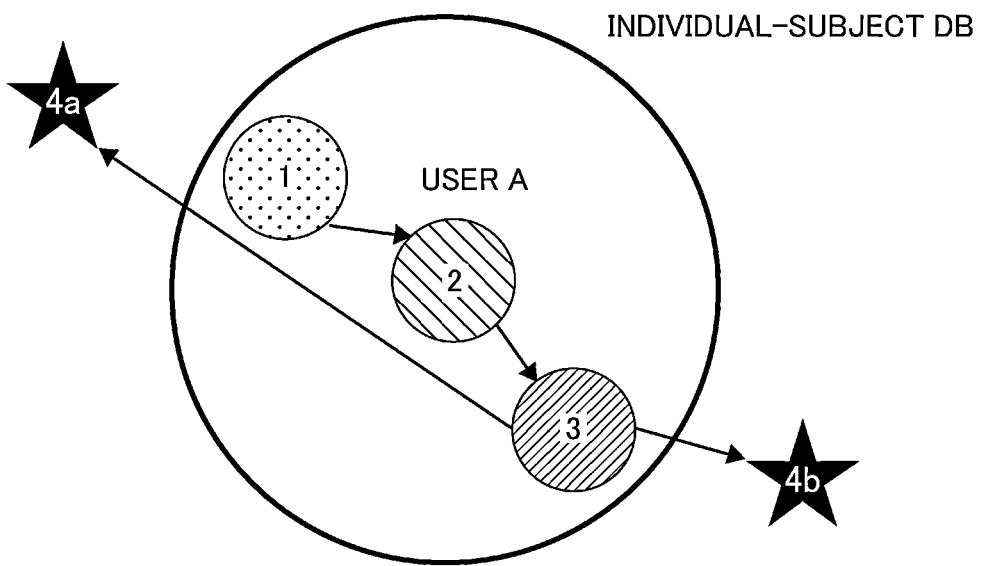
(b)
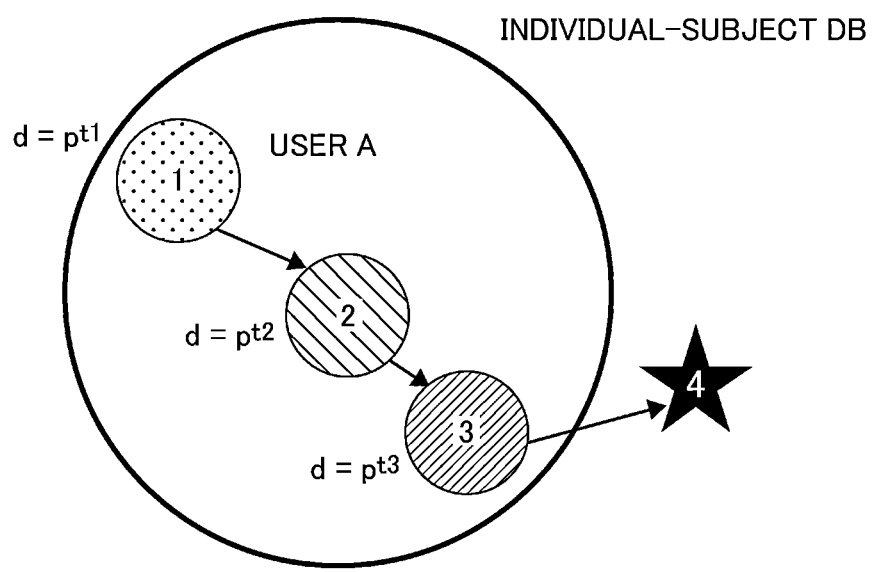

F I G. 1 4

ABNORMALITY DETECTION REASON-PROCESSING CORRESPONDENCE TABLE 50B

| CATEGORY | IDENTIFICATION NUMBER | ABNORMAL DATA DETECTION REASON | ABNORMAL DATA PROCESSING CONTENT |
|---|---|---|---|
| DETECTION OF ABNORMAL DATA WITHOUT USING DB | A | CASE IN WHICH USER CONTINUOUSLY MEASURES SAME TASK BY MISTAKE | USE FIRST MEASUREMENT DATA USE SECOND MEASUREMENT DATA INQUIRE USER OF DATA TO USE |
| | B | CASE IN WHICH TWO-HANDED TASK IS SELECTED BY MISTAKE WHEN ONE-HANDED TASK IS MEASURED | DO NOT USE MEASUREMENT DATA OF HAND HAVING MOTION NON-EXECUTION TIME INQUIRE USER OF HAND USED |
| | C | CASE IN WHICH ONE-HANDED TASK IS SELECTED BY MISTAKE WHEN TWO-HANDED TASK IS MEASURED | |
| | D | CASE IN WHICH TWO-HANDED ALTERNATING FINGER TAP IS SELECTED BY MISTAKE WHEN TWO-HANDED SIMULTANEOUS FINGER TAP IS MEASURED | CHANGE TASK TO TWO-HANDED SIMULTANEOUS FINGER TAP INQUIRE USER OF TASK PERFORMED |
| | E | CASE IN WHICH TWO-HANDED SIMULTANEOUS FINGER TAP IS SELECTED BY MISTAKE WHEN TWO-HANDED ALTERNATING FINGER TAP IS MEASURED | CHANGE TASK TO TWO-HANDED SIMULTANEOUS FINGER TAP INQUIRE USER OF TASK PERFORMED |
| | F | CASE IN WHICH TWO FINGERS CROSS DURING MEASUREMENT | DO NOT USE MEASUREMENT DATA AFTER MEASUREMENT ENDS AND PERFORM RE-MEASUREMENT PERFORM MEASUREMENT ENDED DURING MEASUREMENT AGAIN |
| | G | CASE IN WHICH MOTION SENSOR IS DETACHED FROM FINGER DURING MEASUREMENT | |
| | H | CASE IN WHICH MOVEMENT IS STARTED DURING MEASUREMENT TIME | |
| | I | CASE IN WHICH MOVEMENT IS ENDED DURING MEASUREMENT TIME | |
| | J | CASE IN WHICH MOVEMENT IS SUSPENDED DURING MEASUREMENT TIME | |
| DETECTION OF ABNORMAL DATA USING DB | K | CASE IN WHICH NATURE OF MOVEMENT IS CHANGED BY USER'S INTENSION | DO NOT USE MEASUREMENT DATA INQUIRE USER WHETHER NOT TO USE DATA |
| | L | CASE IN WHICH NATURE OF MOVEMENT IS CHANGED BY USER'S PHYSICAL CONDITIONS | |
| | M | CASE IN WHICH SOMEONE IMPERSONATES USER | |
| | ... | ... | |

FIG. 23
(a) CROSS REACHING
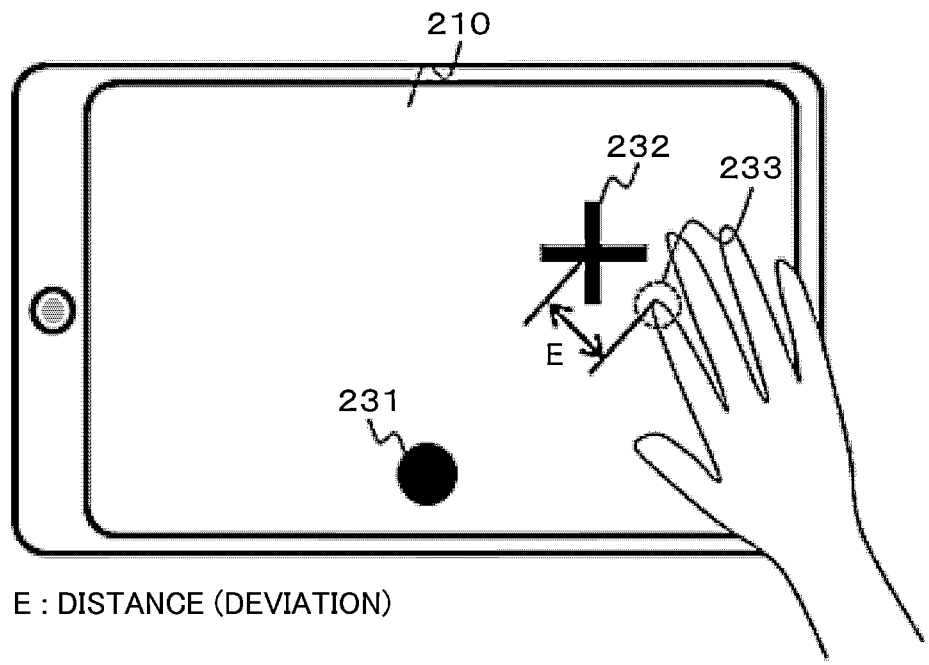
E : DISTANCE (DEVIATION)
(b) CIRCULAR REACHING
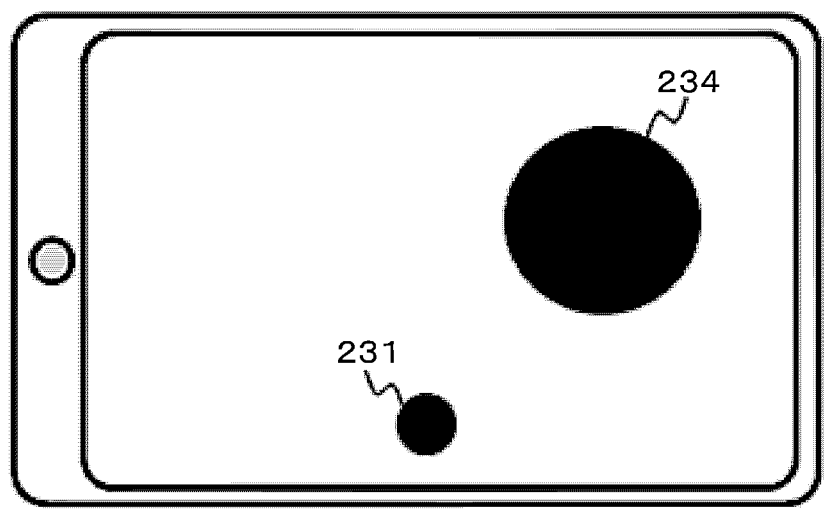

FIG. 24
(a) ONE-HANDED CONTINUOUS TOUCH
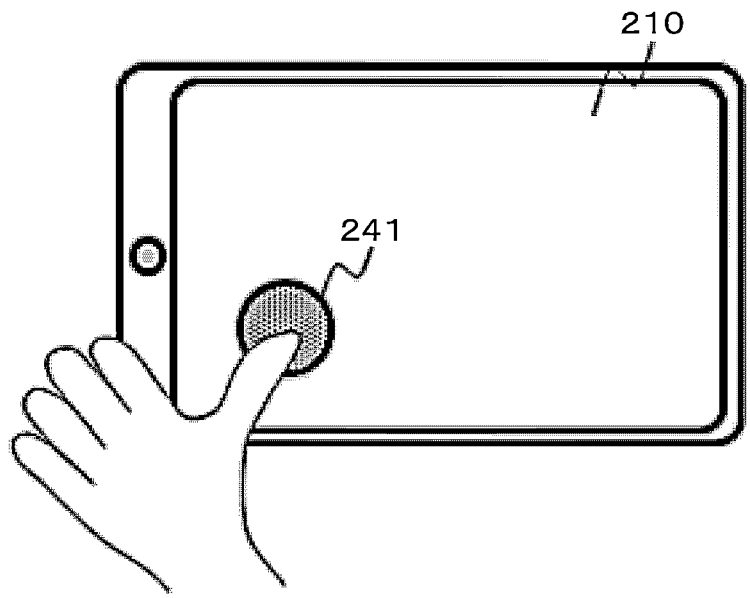
(b) TWO-HANDED SIMULTANEOUS CONTINUOUS TOUCH
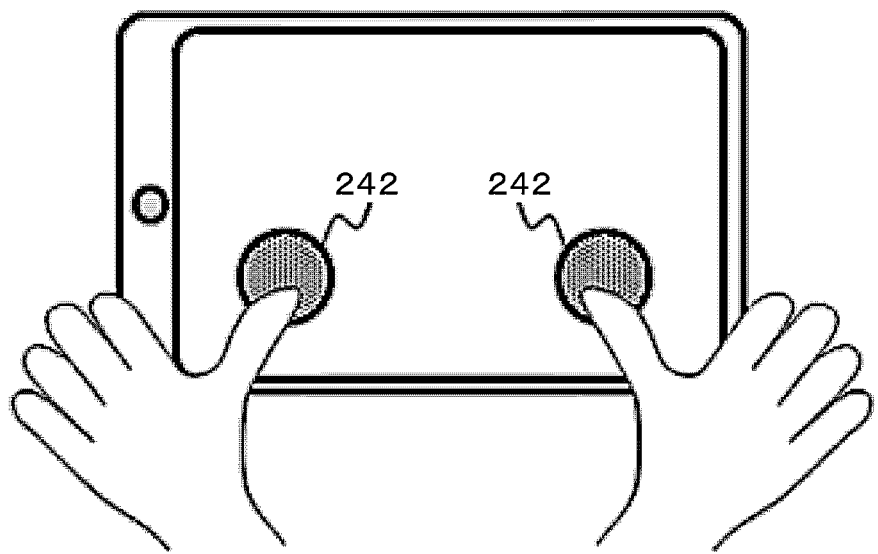

FIG. 25
(a) ONE-HANDED TAP
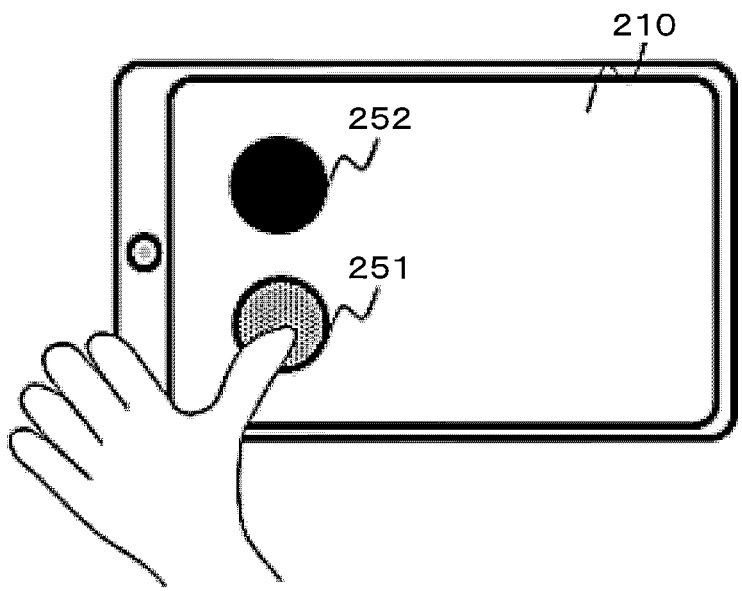
(b) TWO-HANDED SIMULTANEOUS TAP
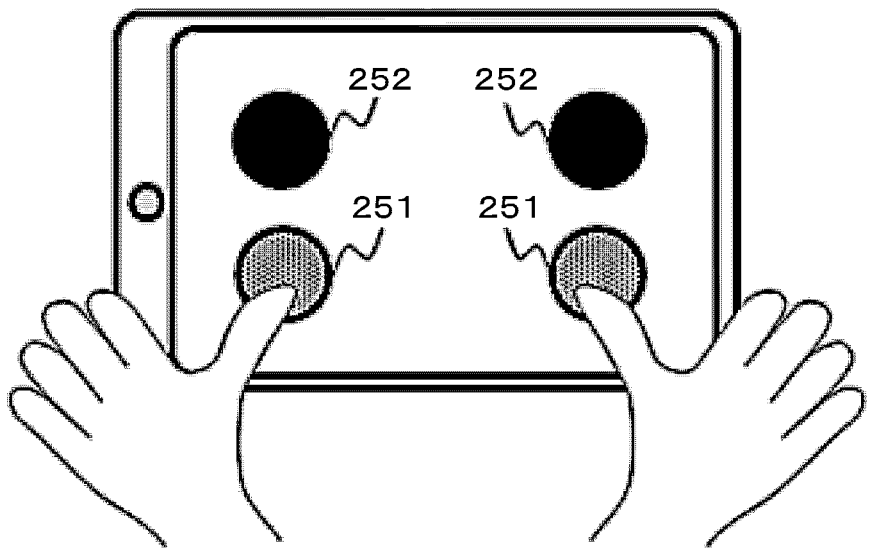

FIVE-FINGER TAP

FIG. 29

USER INFORMATION 41

| USER ID | FACILITY ID | IN-FACILITY USER ID | SEX | AGE | DISEASE | SEVERITY SCORE |
|---|---|---|---|---|---|---|
| 0001 | H001 | ****** | MALE | 55 | DEMENTIA | ~ |
| 0002 | H002 | A**** | FEMALE | 35 | NONE (HEALTHY) | ~ |
| 0003 | H003 | X**** | ... | ... | ... | ... |
| ... | ... | ... | ... | ... | ... | ... |

| SYMPTOM | HISTORY INFORMATION | ... |
|---|---|---|
| ~ | A11<br>{DATE AND TIME<br>MEASUREMENT DATA<br>ANALYSIS EVALUATION DATA<br>ABNORMAL DATA DETECTION RESULT<br>ABNORMAL DATA PROCESSING CONTENT}<br>A12<br>{DATE ......} | ... |
| ~ | A12<br>{DATE ......} | ... |
| ... | ... | ... |
| ... | ... | ... |

ABNORMAL DATA PROCESSING SYSTEM AND ABNORMAL DATA PROCESSING METHOD

TECHNICAL FIELD

The present invention relates to an information processing service technique. Further, the invention relates to a technique for achieving abnormal data processing.

BACKGROUND ART

In fields, such as a healthcare field, a medical field, and a nursing field, human data measurement systems have increased. These systems calculate analysis results from the obtained data and feed the calculation results back to the users to provide value to the users. As an example of the system, there is a system (finger tap measurement and analysis system) which measures and analyzes a finger tapping movement of the user to simply evaluate a cognitive function or a movement function (for example, Patent Document 1). Here, the finger tapping movement is a movement of repeatedly opening and closing the thumb and the index finger. It is known that the performance of the finger tapping movement varies depending on the presence or absence and severity of cerebral dysfunction, such as dementia and Parkinson's disease. It has been pointed out that evaluation, such as early detection or severity estimation of the cerebral dysfunction of the user, is likely to be performed from the analysis results of the finger tapping movement by the above-described system.

CITATION LIST

Patent Document

Patent Document 1: JP 2017-140424 A
Patent Document 2: JP 2013-535268 W
Patent Document 3: JP 2013-039344 A

SUMMARY OF THE INVENTION

Problems to be Solved by the Invention

When a human data measurement service typified by a finger tapping measurement analysis system spreads widely to general households, it is assumed that the measurement is performed by the user alone or by a family who is unfamiliar with the measurement with assistance. When data is measured without a skilled measurer, unreliable data (hereinafter, referred to as "abnormal data") is likely to be measured due to, for example, an inappropriate measurement procedure or the unexpected action of the user.

For example, when the above-mentioned finger tapping measurement and analysis system is given as an example, the following cases are considered: a case in which the user interrupts the finger tapping movement during a predetermined measurement time; and a case in which the user misunderstands an instruction and performs the finger tapping movement.

When the abnormal data is used, there is a problem that it is difficult to feed a highly reliable analysis result back to the user. For example, in the case of the above-mentioned finger tapping measurement and analysis system, it is considered that the performance of the finger tapping movement is regarded as being lower than the actual situation and analysis results indicating that the possibility of cerebral dysfunction is high are obtained even though the possibility of cerebral dysfunction is low originally.

Therefore, a mechanism for automatically processing abnormal data is required. The following cases are considered as approaches to achieve the abnormal data processing mechanism: (A) a case in which abnormality can be detected only by focusing on target data; and (B) a case in which abnormality can be detected for the first time as compared to the past database (DB). In the case of (A), since it is only necessary to have target data, abnormality can be detected by a personal computer (PC) terminal (local PC) connected to a local measurement device. In the case of (B), when the past DB has been stored in a local PC, abnormality can be detected by the local PC. However, when the past DB has been stored in a cloud server, abnormality needs to be detected by the server.

The case of (B) will be described in detail. When the target data is compared with the past DB, the following DBs are considered as the past DB: (i) a DB (hereinafter, referred to as an "individual-subject DB") including only the data of the corresponding user; and (ii) a DB (hereinafter, referred to as a "multiple-subject DB") including the data of many other users. Since the characteristics of the data of the corresponding user are reflected in the individual-subject DB of (i), it is desirable to use the individual-subject DB of (i) in order to accurately detect abnormal data. However, in a case in which the user has already performed the measurement many times, the individual-subject DB of (i) can be used. In a case in which the user has performed the measurement for the first time or only a small number of times, it is necessary to use the multiple-subject DB of (ii) since the DB of (i) is not sufficiently accumulated.

In a case in which the multiple-subject DB of (ii) is used, it is only necessary to accumulate the data of users other than the corresponding user in advance. Therefore, there is an advantage that it is easy to prepare the DB. However, the multiple-subject DB of (ii) is an aggregate of the data of many users and the characteristics of the data of the corresponding user is not reflected in the multiple-subject DB. Therefore, this configuration has a disadvantage that the accuracy of detecting abnormal data is likely to be lower than that in a case in which the individual-subject DB of (i) is used.

From the awareness of the above-mentioned problems, it is considered that a technique which complements the advantages and disadvantages of the individual-subject DB of (i) and the multiple-subject DB of (ii) and uses the two DBs together is needed. Examples of the related art related to abnormal data processing include JP 2013-535268 W (Patent Document 2) and JP 2013-039344 A (Patent Document 3). However, these two patent documents merely disclose a method for specifying whether or not test data is abnormal for a database which has been given in advance and do not disclose a technique that improves the accuracy of detecting abnormal data using both the individual-subject DB and the multiple-subject DB. Therefore, the invention proposes a technique that automatically processes abnormal data with high accuracy.

Solutions to Problems

According to an aspect of the invention, there is provided an abnormal data processing system that detects whether or not new data is abnormal and processes the new data. The abnormal data processing system includes: a storage unit that stores a multiple-subject DB in which data of a plurality of subjects is accumulated and an individual-subject DB in which data of an individual subject is accumulated; an individual-subject DB divergence degree calculation unit that calculates an individual-subject DB divergence degree which is a degree of divergence of the new data from the individual-subject DB; a multiple-subject DB divergence degree calculation unit that calculates a multiple-subject DB divergence degree which is a degree of divergence of the new data from the multiple-subject DB; and a composite divergence degree calculation unit that calculates a composite degree of divergence obtained by combining the individual-subject DB divergence degree and the multiple-subject DB divergence degree, using the number of data items in the individual-subject DB. It is determined whether or not the new data is abnormal on the basis of the composite degree of divergence. There is provided an abnormal data processing method that detects whether or not new data acquired by an input unit is abnormal and processes the new data, using the input unit, an output unit, a control unit, and a storage unit. The abnormal data processing method includes: storing a multiple-subject DB in which data of a plurality of subjects is accumulated and an individual-subject DB in which data of an individual subject is accumulated in the storage unit; calculating an individual-subject DB divergence degree which is a degree of divergence of the new data from the individual-subject DB; calculating a multiple-subject DB divergence degree which is a degree of divergence of the new data from the multiple-subject DB; calculating a composite degree of divergence using the individual-subject DB divergence degree and the multiple-subject DB divergence degree, on the basis of the number of data items in the individual-subject DB; and determining whether or not the new data is abnormal on the basis of the composite degree of divergence.

Effects of the Invention

It is possible to achieve a technique that automatically processes abnormal data with high accuracy.

BRIEF DESCRIPTION OF THE DRAWINGS

FIG. 6 is a block diagram illustrating the configuration of a motion sensor control unit and the like of the measurement device in Embodiment 1.

FIG. 9 is a table illustrating an example of the configuration of a feature amount list in Embodiment 1.

FIG. 10 is a waveform diagram illustrating an example of non-DB-using abnormal data detection in Embodiment 1.

FIG. 12 is a conceptual diagram illustrating a method for calculating a composite degree of divergence in Embodiment 1.

FIG. 13 is a conceptual diagram illustrating a method for calculating a degree of divergence in consideration of a time series in Embodiment 1.

FIG. 14 is a table illustrating an example of the configuration of an abnormality detection reason-processing correspondence table in Embodiment 1.

FIG. 23 is a plan view illustrating reaching as an example of the movement in Embodiment 2.

FIG. 24 is a plan view illustrating a continuous touch as an example of the movement in Embodiment 2.

FIG. 25 is a plan view illustrating a tap according to stimulation as an example of the movement in Embodiment 2.

FIG. 29 is a table illustrating an example of the configuration of user information which is server management information in Embodiment 3.

MODE FOR CARRYING OUT THE INVENTION

Figure 1:
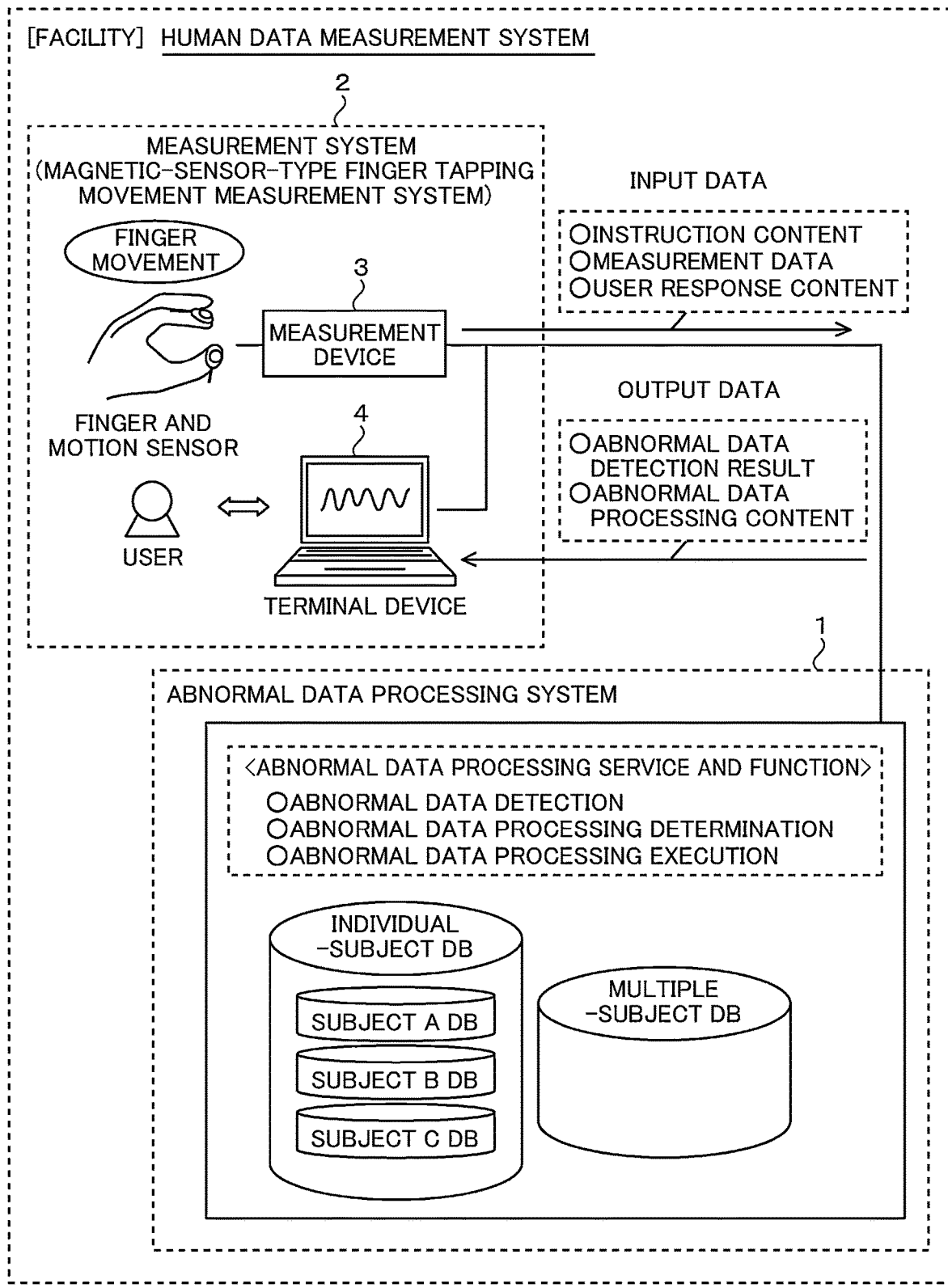
FIG. 1 is a block diagram illustrating the configuration of an abnormal data processing system according to Embodiment 1 of the present invention.

Hereinafter, embodiments of the invention will be described in detail with reference to the drawings. In all the drawings for describing the embodiments, the same portions are denoted by the same reference numerals in principle and the description thereof will not be repeated.

The embodiments will be described in detail with reference to the drawings. The invention is not construed as being limited to the description of the following embodiments. It is easily understood by those skilled in the art that a specific configuration can be changed without departing from the spirit or spirit of the invention.

In a case in which there are a plurality of elements having the same or similar functions, the same reference numerals may be given different subscripts for explanation. However, in a case in which there is no need to distinguish a plurality of elements, the description of the elements may be made with suffixes omitted.

For example, notations, such as "first", "second", and "third", in the specification are used to identify components and do not necessarily limit the number, order, or content thereof. In addition, numbers for identifying components are used for each context and numbers used in one context do not necessarily indicate the same configuration in another context. Further, a component identified by one number may also have the function of a component identified by another number.

For example, in some cases, the position, size, shape, and range of each component illustrated in the drawings are different from the actual position, size, shape, and range for ease of understanding of the invention. Therefore, the invention is not necessarily limited to, for example, the position, size, shape, and range disclosed in the drawings.

In this embodiment, a technique for automatically processing abnormal data is proposed. In the processing of abnormal data, there are the following cases: (A) a case in which abnormality can be detected only by focusing on target data; and (B) a case in which abnormality can be detected for the first time as compared to the past DB. In this embodiment, particularly, for (B), a technique is proposed which detects abnormal data using both (i) a DB (individual-subject DB) including only the data of the corresponding user and (ii) a DB (multiple-subject DB) including the data of many other users. According to a typical embodiment, (i) a decrease in accuracy due to an insufficient amount of data when the DB including only of the data of the user is used and a decrease in accuracy due to incapability to reflect an individual difference when the DB including the data of many other users is used are complemented to detect abnormal data with high accuracy.

Embodiment 1

An abnormal data processing system according to Embodiment 1 of the invention will be described with reference to FIGS. 1 to 19. The abnormal data processing system according to Embodiment 1 has a function of detecting abnormality in data measured by a user and generating processing content in a case in which abnormality is detected. This function makes it possible to detect abnormal data with high accuracy.

[Human Data Measurement System (1)]

FIG. 1 illustrates the configuration of a human data measurement system including the abnormal data processing system according to Embodiment 1. In Embodiment 1, a human data measurement system is provided in a facility, such as a hospital or a facility for the elderly, or in the user's home. The human data measurement system includes an abnormal data processing system 1 and a measurement system 2 which is a magnetic-sensor-type finger tapping movement system and these systems are connected to each other through a communication line. The measurement system includes a measurement device 3 and a terminal device 4 which are connected to each other through a communication line. A plurality of measurement systems 2 may be provided in the facility.

The measurement system 2 is a system that measures finger movement using a magnetic-sensor-type motion sensor. A motion sensor is connected to the measurement device 3. The motion sensor is attached to the user's finger. The measurement device 3 measures finger movement through the motion sensor to obtain measurement data including a time-series waveform signal.

The terminal device 4 displays various kinds of information for abnormal data processing including the detection result of abnormal data, a reason for abnormality detection, and the content of abnormal data processing on a display screen and receives an operation input by the user. In Embodiment 1, the terminal device 4 is a PC.

The abnormal data processing system 1 has a function of providing an abnormal data processing service as an information processing service. For example, the abnormal data processing system 1 has, as its functions, an abnormal data detection function and an abnormal data processing determination function. The abnormal data detection function is a function of detecting whether or not measurement data measured by the measurement system 2 is abnormal. The abnormal data processing determination function is a function of determining a process for the data in which abnormality has been detected by the abnormal data detection function.

The abnormal data processing system 1 receives, for example, the content of an instruction to the user and measurement data as input data from the measurement system 2. The abnormal data processing system 1 outputs, for example, the detection result of abnormal data and the content of abnormal data processing as output data to the measurement system 2. The detection result of abnormal data includes a reason for abnormal data detection in addition to whether or not the measurement data is abnormal.

The human data measurement system according to Embodiment 1 can be widely applied to general facilities and people in addition to facilities, such as hospitals and facilities for the elderly, and subjects in the facilities. The measurement device 3 and the terminal device 4 may be integrated into a measurement system. The measurement system 2 and the abnormal data processing system 1 may be integrated into an apparatus. The terminal device 4 and the abnormal data processing system 1 may be integrated into an apparatus. The measurement device 3 and the abnormal data processing system 1 may be integrated into an apparatus.

[Abnormal Data Processing System]

Figure 2:
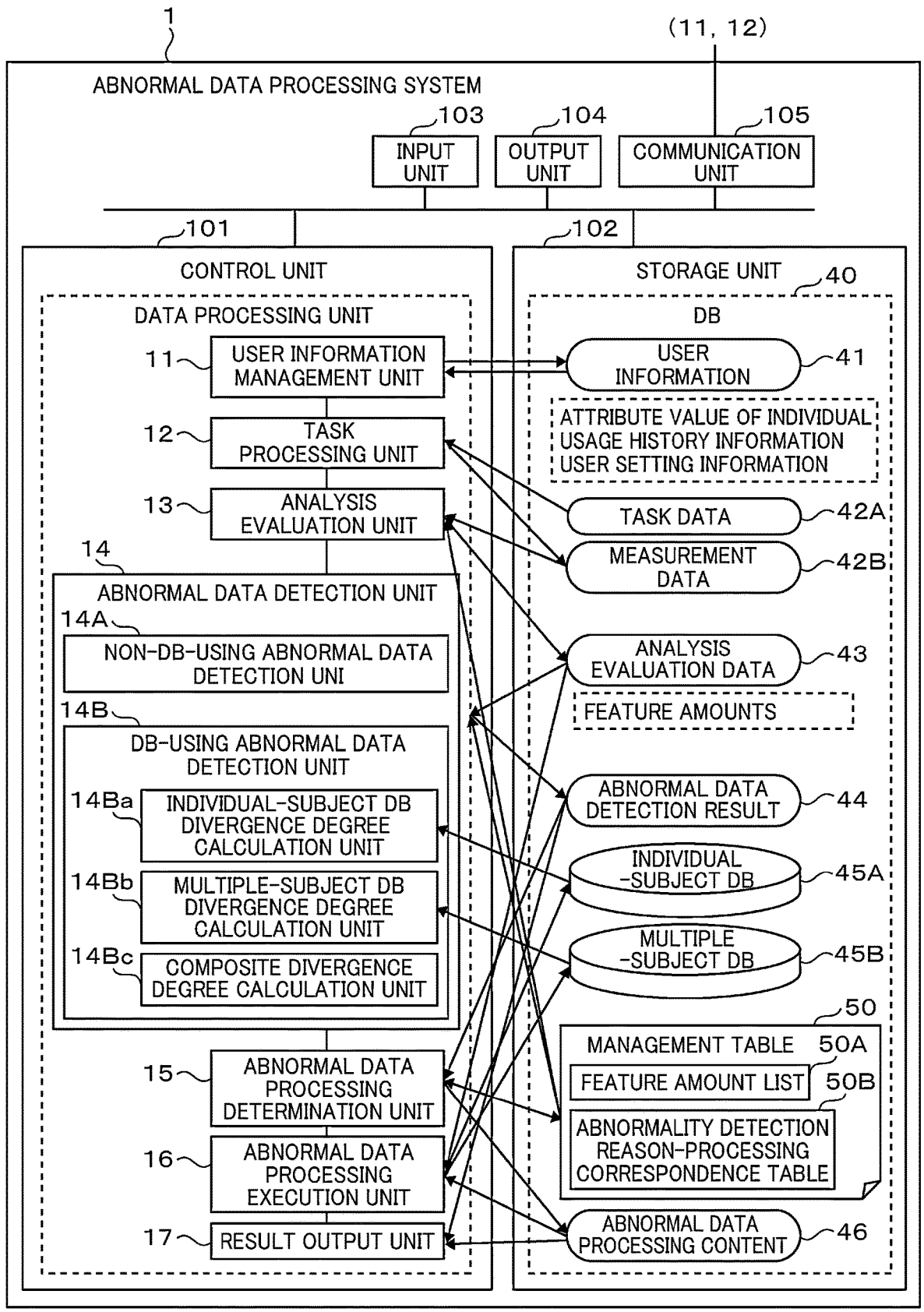
FIG. 2 is a block diagram illustrating the configuration of the abnormal data processing system in Embodiment 1.

FIG. 2 illustrates the configuration of the abnormal data processing system 1 according to Embodiment 1. The abnormal data processing system 1 includes, for example, a control unit 101, a storage unit 102, an input unit 103, an output unit 104, and a communication unit 105 which are connected to each other through a bus. The input unit 103 is a portion that inputs an operation of, for example, the administrator of the abnormal data processing system 1. The output unit 104 is a portion that displays a screen to, for example, the administrator of the abnormal data processing system 1. The communication unit 105 has a communication interface and performs a communication process with the measurement device 3 and the terminal device 4.

The control unit 101 controls the entire abnormal data processing system and includes, for example, a central processing unit (CPU), a read only memory (ROM), a random access memory (RAM) and implements a data processing unit that performs, for example, abnormal data detection or abnormal data processing determination on the basis of software program processing. A data processing unit of the control unit 101 includes a user information management unit 11, a task processing unit 12, an analysis evaluation unit 13, an abnormal data detection unit 14, an abnormal data processing determination unit 15, an abnormal data processing execution unit 16, and a result output unit 17. The control unit 101 implements, for example, a function of receiving measurement data from the measurement device 3, a function of processing and analyzing the measurement data, a function of outputting a control instruction to the measurement device 3 or the terminal device 4, and a function of outputting display data to the terminal device 4.

The user information management unit 11 performs, for example, a process of registering user information input by the user in user information 41 of a DB 40 and managing the user information and a process of checking the user information 41 of the DB 40 when the user uses a service. The user information 41 includes, for example, attribute values, usage history information, user setting information for each user. The attribute values include, for example, sex and age. The usage history information is information for managing the history of the user using the service provided by the system. The user setting information is setting information set by the user for the function of the service.

The task processing unit 12 is a portion that performs a process related to a task for analyzing and evaluating, for example, a movement function. In other words, the task is a predetermined finger movement. The task processing unit 12 outputs a task to the screen of the terminal device 4 on the basis of task data 42A in the DB 40. Further, the task processing unit 12 acquires the measurement data of the task measured by the measurement device 3 and stores the measurement data as measurement data 42B in the DB 40.

The analysis evaluation unit 13 is a portion that calculates a feature amount indicating the property of the measurement data on the basis of the measurement data 42B of the user. The analysis evaluation unit 13 stores analysis evaluation data 43 which is the result of an analysis evaluation process in the DB 40.

The abnormal data detection unit 14 performs a process of detecting abnormal data and a process of outputting abnormal data detection result 44 to the screen of the terminal device 4, on the basis of the analysis evaluation data 43 of the user, an individual-subject DB 45A, a multiple-subject DB 45B, and information of an abnormality detection reason-processing correspondence table 50B in a management table 50. The abnormal data detection unit 14 stores the detection result of abnormality as the abnormal data detection result 44 in the DB 40. The abnormal data detection result 44 includes the reason for abnormal data detection in addition to whether or not the measurement data is abnormal. The abnormal data detection unit 14 transmits the abnormal data detection result 44 of the DB 40 to the terminal device 4 so as to be output to the screen. The abnormal data detection unit 14 includes a non-DB-using abnormal data detection unit 14A that detects abnormal data without using a DB and a DB-using abnormal data detection unit 14B that detects abnormal data using a DB. The DB-using abnormal data detection unit 14B includes an individual-subject DB divergence degree calculation unit 14Ba, a multiple-subject DB divergence degree calculation unit 14Bb, and a composite divergence degree calculation unit 14Bc.

The abnormal data processing determination unit 15 performs, for example, a process of creating abnormal data processing content 46 on the basis of the abnormal data detection result 44 and the abnormality detection reason-processing correspondence table 50B in the management table 50 and storing the abnormal data processing content 46 in the DB 40.

The abnormal data processing execution unit 16 performs, for example, a process of executing abnormal data processing content on the basis of the abnormal data processing content 46. At this time, the measurement data 42B may or may not be stored in the individual-subject DB 45A or the multiple-subject DB 45B according to the abnormal data processing content 46.

Here, the individual-subject DB 45A is a DB including only the data of a specific user and the multiple-subject DB 45B is a DB obtained by combining the data of a plurality of users. In general, the data of the individual-subject DB 45A is a subset of the multiple-subject DB 45B. However, the data of the individual-subject DB 45A may not be necessarily included in the data of the multiple-subject DB 45B. In addition, the individual-subject DB 45A and the multiple-subject DB 45B may be separated as databases. However, information for specifying a user may be attached to the data of the multiple-subject DB 45B such that the data of a specific user can be extracted. In this case, the multiple-subject DB 45B can also have the functions of the individual-subject DB 45A.

The result output unit 17 performs a process of outputting the analysis and evaluation data 43 of the user, the abnormal data detection result 44, and the abnormal data processing content 46 to the screen of the terminal device 4. The analysis evaluation unit 13, the abnormal data detection unit 14, the abnormal data processing determination unit 15, and the abnormal data processing execution unit 16 perform a screen output process in cooperation with the result output unit 17.

Examples of the data and information stored in the DB 40 of the storage unit 102 include the user information 41, the task data 42A, the measurement data 42B, the analysis evaluation data 43, the abnormal data detection result 44, the individual-subject DB 45A, the multiple-subject DB 45B, the abnormal data processing content 46, and the management table 50. The control unit 101 stores the management table 50 in the storage unit 102 and manages the management table 50. The administrator can set the content of the management table 50. The management table 50 stores, for example, a feature amount list 50A for setting feature amounts and the abnormality detection reason-processing correspondence table 50B for setting a process corresponding to the abnormality detection reason.

[Measurement Device]

Figure 3:
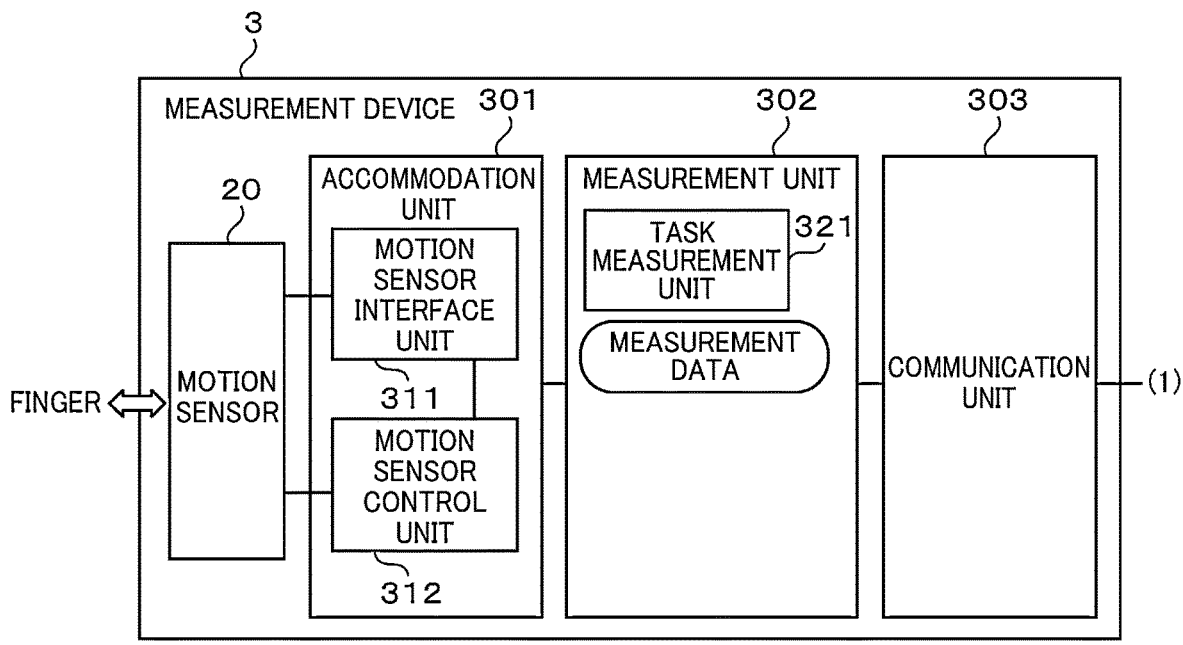
FIG. 3 is a block diagram illustrating the configuration of a measurement device in Embodiment 1.

FIG. 3 illustrates the configuration of the measurement device 3 according to Embodiment 1. The measurement device 3 includes, for example, a motion sensor 20, an accommodation unit 301, a measurement unit 302, and a communication unit 303. The accommodation unit 301 includes a motion sensor interface unit 311 to which the motion sensor 20 is connected and a motion sensor control unit 312 that controls the motion sensor 20. The measurement unit 302 measures a waveform signal through the motion sensor 20 and the accommodation unit 301 and outputs the measured signal as measurement data. The measurement unit 302 includes a task measurement unit 321 that obtains measurement data. The communication unit 303 has a communication interface and communicates with the abnormal data processing system 1 to transmit measurement data to the abnormal data processing system 1. The motion sensor interface unit 311 includes an analog-to-digital conversion circuit and converts an analog waveform signal detected by the motion sensor 20 into a digital waveform signal using sampling. The digital waveform signal is input to the motion sensor control unit 312.

The measurement device 3 may store each measurement data item in the storage unit. Alternatively, the measurement device 3 may not store each measurement data item and only the abnormal data processing system 1 may store each measurement data item.

[Terminal Device]

Figure 4:
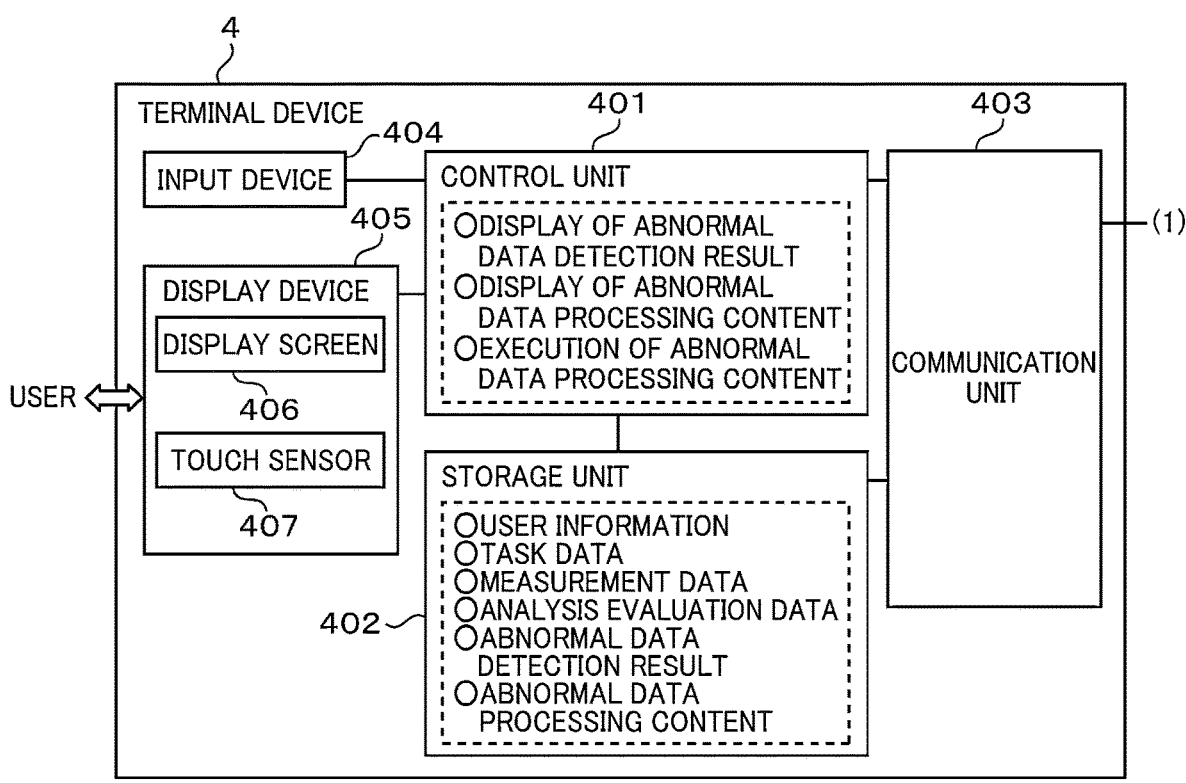
FIG. 4 is a block diagram illustrating the configuration of a terminal device in Embodiment 1.

FIG. 4 illustrates the configuration of the terminal device 4 according to Embodiment 1. The terminal device 4 includes a control unit 401, a storage unit 402, a communication unit 403, an input device 404, and a display device 405. The control unit 401 performs, for example, the display of abnormal data detection results, the display of abnormal data processing content, and the execution of abnormal data processing content, as control processes based on software program processing. The storage unit 402 stores, for example, the user information, the task data, the measurement data, the analysis evaluation data, the abnormal data detection results, and the abnormal data processing content obtained from the abnormal data processing system 1. The communication unit 403 has a communication interface and communicates with the abnormal data processing system 1 to receive various kinds of data from the abnormal data processing system 1 and to transmit, for example, user instruction input information to the abnormal data processing system 1. The input device 404 is, for example, a keyboard or a mouse. The display device 405 displays various kinds of information on a display screen 406. In addition, the display device 405 may be a touch panel.

[Finger, Motion Sensor, and Finger Tap Measurement]

Figure 5:
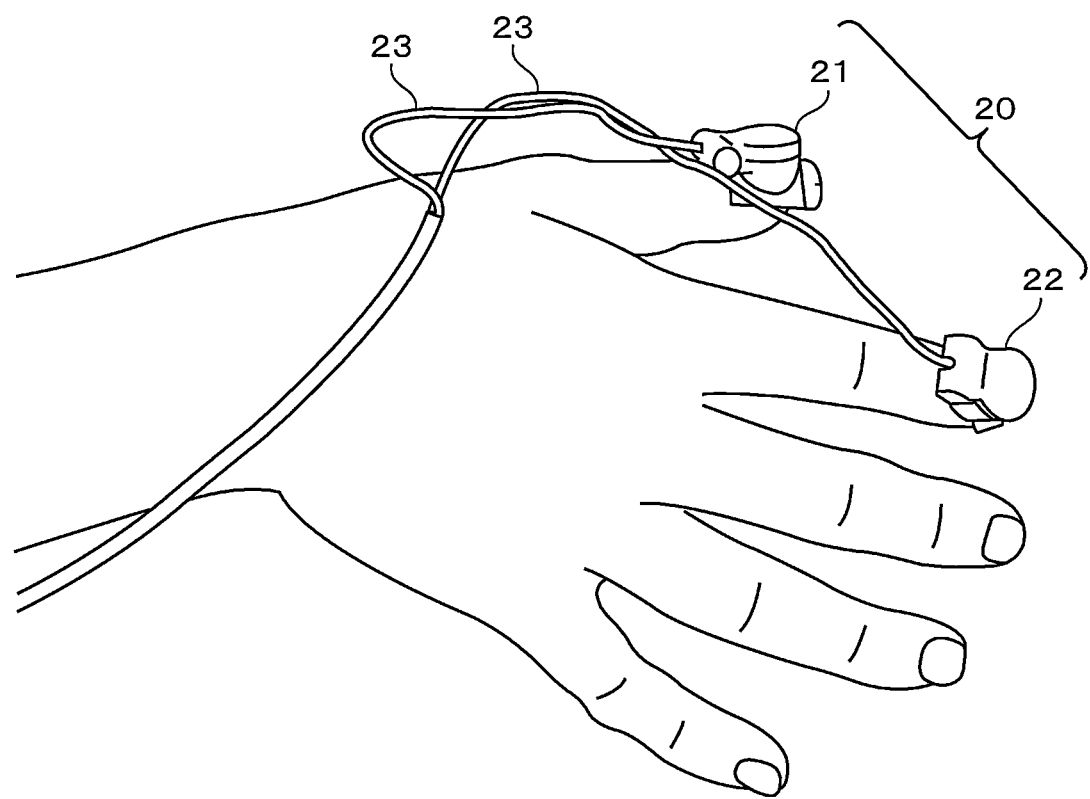
FIG. 5 is a perspective view illustrating a motion sensor attached to a finger in Embodiment 1.

FIG. 5 illustrates a state in which a magnetic sensor, which is the motion sensor 20, is attached to the user's finger. The motion sensor 20 has a transmitting coil unit 21 and a receiving coil unit 22 which are paired coil units and are connected to the measurement device 3 through signal lines 23. The transmitting coil unit 21 generates a magnetic field and the receiving coil unit 22 detects the magnetic field. In the example illustrated in FIG. 5, in the right hand of the user, the transmitting coil unit 21 is attached to the vicinity of the nail of the thumb and the receiving coil unit 22 is attached to the vicinity of the nail of the index finger. The fingers to which the coil units are attached can be changed to other fingers. The place to which the coil unit is attached is not limited to the vicinity of the nail.

As illustrated in FIG. 5, it is assumed that the motion sensor 20 is attached to the target finger of the user, for example, two fingers of the left thumb and the index finger.

In this state, the user performs a finger tap which is the repetitive movement of opening and closing two fingers. In the finger tap, movement is performed between a state in which two fingers are closed, that is, a state in which the tips of two fingers come into contact with each other, and a state in which two fingers are opened, that is, a state in which the tips of two fingers are opened. The distance between the coil units, that is, the transmitting coil unit 21 and the receiving coil unit 22 which corresponds to the distance between the tips of two fingers is changed by this movement.

The measurement device 3 measures a waveform signal corresponding to a change in the magnetic field between the transmitting coil unit 21 and the receiving coil unit 22 of the motion sensor 20.

The finger tap includes the following various types of tasks in detail. Examples of the movement include one-handed free-run, one-handed metronome, two-handed simultaneous free-run, two-handed alternating free-run, two-handed simultaneous metronome, two-handed alternating metronome. The one-handed free-run means performing finger tapping with two fingers of one hand several times as quickly as possible. The one-handed metronome means performing finger tapping with two fingers of one hand in synchronization with a constant pace of stimulation. The two-handed simultaneous free-run means performing finger tapping at the same timing with two fingers of the left hand and two fingers of the right hand. The two-handed alternating free-run means performing finger tapping at an alternate timing with two fingers of the left hand and two fingers of the right hand.

[Motion Sensor Control Unit and Finger Tap Measurement]

FIG. 6 illustrates an example of the detailed configuration of, for example, the motion sensor control unit 312 of the measurement device 3. In the motion sensor 20, the distance between the transmitting coil unit 21 and the receiving coil unit 22 is represented by D. The motion sensor control unit 312 includes an alternating current generation circuit 312a, a current generation amplifier circuit 312b, a pre-amplifier circuit 312c, a detection circuit 312d, an LPF circuit 312e, a phase adjustment circuit 312f, an amplifier circuit 312g, and an output signal terminal 312h. The alternating current generation circuit 312a is connected to the current generation amplifier circuit 312b and the phase adjustment circuit 312f. The transmitting coil unit 21 is connected to the current generation amplifier circuit 312b through the signal line 23. The receiving coil unit 22 is connected to the pre-amplifier circuit 312c through the signal line 23. The detection circuit 312d, the LPF circuit 312e, the amplifier circuit 312g, and the output signal terminal 312h are sequentially connected to a stage behind the pre-amplifier circuit 312c. The detection circuit 312d is connected to the phase adjustment circuit 312f.

The alternating current generation circuit 312a generates an alternating current voltage signal with a predetermined frequency. The current generation amplifier circuit 312b converts the alternating current voltage signal into an alternating current with a predetermined frequency and outputs the alternating current to the transmitting coil unit 21. The transmitting coil unit 21 generates a magnetic field using the alternating current. The magnetic field causes the receiving coil unit 22 to generate an induced electromotive force. The receiving coil unit 22 outputs an alternating current generated by the induced electromotive force. The frequency of the alternating current is equal to the predetermined frequency of the alternating current voltage signal generated by the alternating current generation circuit 312a.

The pre-amplifier circuit 312c amplifies the detected alternating current. The detection circuit 312d detects the amplified signal on the basis of a reference signal 312i from the phase adjustment circuit 312f. The phase adjustment circuit 312f adjusts the phase of the alternating current voltage signal with a predetermined frequency or a frequency that is twice the predetermined frequency which has been transmitted from the alternating current generation circuit 312a and outputs the alternating current voltage signal as the reference signal 312i. The LPF circuit 312e limits the band of the detected signal and outputs the signal. The amplifier circuit 312g amplifies the signal to a predetermined voltage. Then, an output signal corresponding to the measured waveform signal is output from the output signal terminal 312h.

The waveform signal which is the output signal is a signal having a voltage value indicating the distance D between two fingers. The distance D and the voltage value can be converted on the basis of a predetermined calculation expression. The calculation expression may be obtained by calibration. In the calibration, for example, measurement is performed in a state in which the user holds a block with a predetermined length with two fingers of a target hand. A predetermined calculation expression is obtained as an approximate curve that minimizes an error from a data set of the voltage value and the distance value in the measured value.

Further, the size of the user's hand may be checked by calibration and may be used for, for example, normalizing feature amounts. In Embodiment 1, the above-mentioned magnetic sensor is used as the motion sensor 20 and a measurement means corresponding to the magnetic sensor is used. However, the invention is not limited thereto. For example, other detection means and measurement means, such as an acceleration sensor, a strain gauge, and a high-speed camera, may be applied.

[Process Flow]

Figure 7:
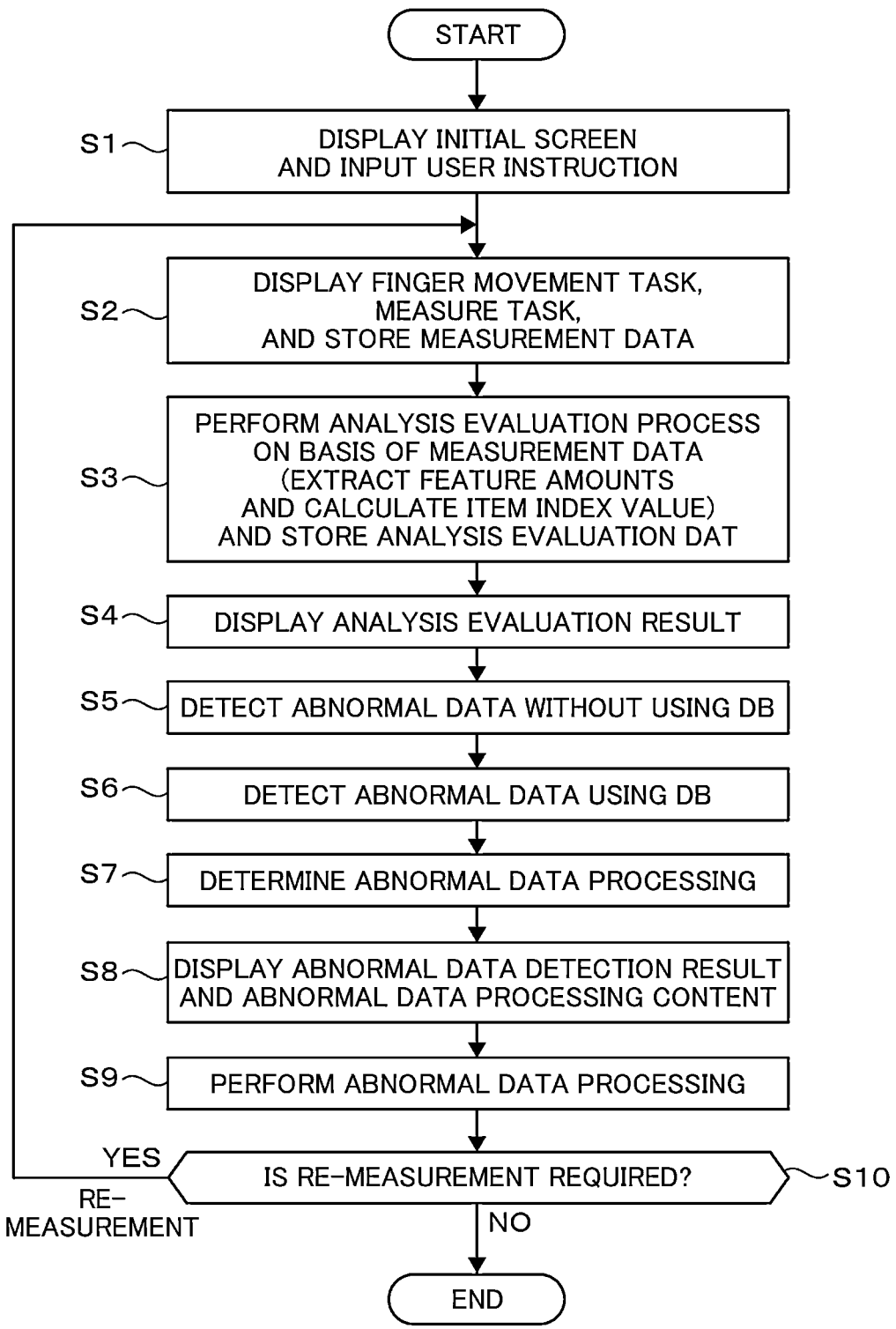
FIG. 7 is a flowchart illustrating a process flow of the abnormal data processing system in Embodiment 1.

FIG. 7 illustrates the flow of the entire process which is mainly performed by the abnormal data processing system 1 in the human data measurement system according to Embodiment 1. FIG. 7 has Steps S1 to S10. Hereinafter, the process will be described in the order of the steps.

(S1) The user operates the measurement system 2. The terminal device 4 displays an initial screen on the display screen. The user selects a desired operation item on the initial screen. For example, an operation item for detecting and processing abnormal data is selected. The terminal device 4 transmits instruction input information corresponding to the selection to the abnormal data processing system 1. In addition, the user can input and register user information, such as sex and age, on the initial screen. In this case, the terminal device 4 transmits the input user information to the abnormal data processing system 1. The user information management unit 11 of the abnormal data processing system 1 registers the user information in the user information 41.

(S2) The task processing unit 12 of the abnormal data processing system transmits task data for the user to the terminal device 4 on the basis of the instruction input information of S1 and the task data 42A of the finger tap. The task data includes one or more kinds of task information related to finger movement, such as one-handed free-run, two-handed simultaneous free-run, and two-handed alternating free-run. The terminal device 4 displays finger movement task information on the display screen on the basis of the received task data. The user performs a finger movement task according to the task information on the display screen. The measurement device 3 measures the task and transmits the task as measurement data to the abnormal data processing system 1. The abnormal data processing system 1 stores the measurement data in the measurement data 42B.

(S3) The analysis evaluation unit 13 of the abnormal data processing system performs a process of analyzing and evaluating, for example, the user's movement function on the basis of the measurement data 42B of S2 to create the analysis evaluation data 43 of the user and stores the analysis evaluation data 43 in the DB 40. In the analysis evaluation process, the analysis evaluation unit 13 extracts feature amounts on the basis of the waveform signal of the measurement data 42B of the user. The feature amounts include, for example, feature amounts calculated from a distance waveform which will be described below and feature amounts calculated from a velocity waveform. The feature amounts are recorded on the feature amount list 50A. The analysis evaluation unit 13 may correct the extracted feature amounts on the basis of an attribute value such as the age of the user. Then, the corrected feature amounts may be used for evaluation.

(S4) The result output unit 17 of the abnormal data processing system 1 outputs analysis evaluation result information to the display screen of the terminal device 4 on the basis of the analysis evaluation data 43 of S3. The user can check the analysis evaluation result information indicating the state of, for example, his or her movement function on the display screen. Step S4 may be omitted.

(S5) The non-DB-using abnormal data detection unit 14A in the abnormal data detection unit 14 of the abnormal data processing system 1 detects abnormal data without using the DB on the basis of the analysis evaluation data 43 of S3. That is, the non-DB-using abnormal data detection unit 14A detects abnormality that can be detected only from the measurement data, without referring to the individual-subject DB 45A or the multiple-subject DB 45B which was accumulated in the past. A detailed detection method will be described below. A list of abnormality detection reasons to be detected is recorded on the abnormality detection reason-processing correspondence table 50B. Abnormal data is detected on the basis of the abnormality detection reason. The result is stored in the abnormal data detection result 44 of the storage unit 40. Step S5 may be omitted and only Step S6 may be performed.

(S6) The DB-using abnormal data detection unit 14B in the abnormal data detection unit 14 of the abnormal data processing system 1 detects abnormal data using the DB on the basis of the analysis evaluation data 43 of S3, the individual-subject DB 45A, and the multiple-subject DB 45B. That is, the measurement data is compared with the past individual-subject DB or multiple-subject DB to detect abnormality that can be detected first. A detailed detection method will be described below. A list of abnormality detection items to be detected is recorded on the abnormality detection reason-processing correspondence table 50B. Abnormal data is detected on the basis of the abnormality detection item. The result is stored in the abnormal data detection result 44 of the storage unit 40. Step S6 may be omitted and only Step S5 may be performed.

(S7) The abnormal data processing determination unit 15 of the abnormal data processing system 1 determines the abnormal data processing content 46 on the basis of the abnormal data detection result 44 generated in Steps S5 and S6. A detailed determination method will be described below. A correspondence table between the abnormal data detection result 44 and the abnormal data processing content 46 is recorded on the abnormality detection reason-processing correspondence table 50B. The abnormal data processing determination unit 15 determines abnormal data processing content on the basis of the correspondence table and stores the abnormal data processing content in the abnormal data processing content 46.

(S8) In the abnormal data processing system 1, the analysis and evaluation unit 13 displays the abnormal data detection result 44 generated in S5 and S6 and the abnormal data processing content 46 generated in S7 on the display screen. The user can check the current detection result of abnormal data and the processing content thereof on the display screen.

(S9) The abnormal data processing system 1 performs abnormal data processing on the basis of the abnormal data processing content 46. As an example, a process is considered which stores the abnormal data processing content in the individual-subject DB 45A and the multiple-subjects DB 45B in a case in which abnormality has not been detected and does not store the abnormal data processing content in a case in which abnormality has been detected. As another example, a process is considered which outputs the abnormal data processing content 46 to the terminal device 4 through the communication unit 105 to request re-measurement. A detailed execution method will be described below.

(S10) In a case in which the re-measurement request is transmitted to the terminal device 4 in S9, the abnormal data processing system 1 returns to S2 and repeats the process in the same manner. In a case in which the re-measurement request is not transmitted, the flow ends.

[Feature Amounts]

Figure 8:
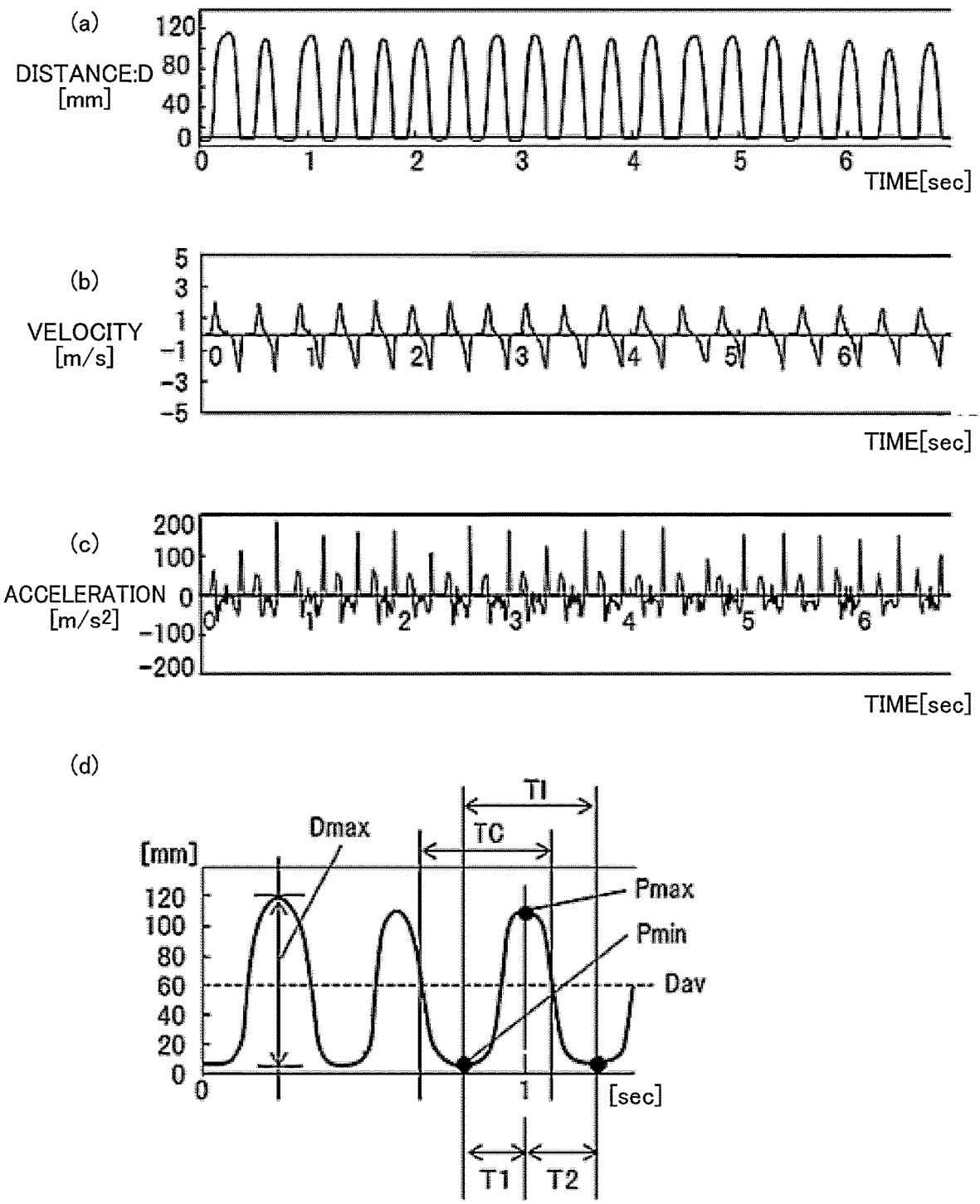
FIG. 8 is a waveform diagram illustrating an example of waveform signals of feature amounts in Embodiment 1.

FIG. 8 illustrates an example of the waveform signals of the feature amounts. In FIG. 8, (a) illustrates a waveform signal of the distance D between two fingers, (b) illustrates a waveform signal of the velocity of two fingers, and (c) illustrates a waveform signal of the acceleration of two fingers. The velocity in (b) is obtained by the time differentiation of the waveform signal of the distance in (a). The acceleration in (c) is obtained by the time differentiation of the waveform signal of the velocity in (b). The analysis evaluation unit 13 obtains the waveform signals of predetermined feature amounts in this example from the waveform signal of the measurement data 42B on the basis of an operation, such as differentiation or integration. Further, the analysis evaluation unit 13 obtains predetermined calculated values from the feature amounts.

(d) of FIG. 8 is an enlarged view of (a) and illustrates an example of the feature amount. (d) of FIG. 8 illustrates, for example, a maximum value Dmax of the finger tap distance D and a tap interval TI. A horizontal dashed line indicates an average value Dav of the distance D over the entire measurement time. The maximum value Dmax indicates the maximum value of the distance D over the entire measurement time. The tap interval TI is the time corresponding to the cycle TC of one finger tap and particularly indicates the time from a local minimum point Pmin to the next local minimum point Pmin. In addition, (d) of FIG. 8 illustrates a local maximum point Pmax, the local minimum point Pmin within one cycle of the distance D, the time T1 of an opening operation which will be described below, and the time T2 of a closing operation will be described below.

Hereinafter, a detailed example of the feature amounts will be described. In Embodiment 1, a plurality of feature amounts obtained from the waveforms of the distance, the velocity, and the acceleration are used. In other embodiments, only some of the plurality of feature amounts may be used or other feature amounts may be used. The details of the definition of the feature amounts are not limited.

FIG. 9 illustrates a feature amount [distance] among the finger tap feature amounts recorded on the feature amount list 50A. The setting of this association is an example and can be changed. The feature amount list 50A illustrated in FIG. 9 has a feature amount classification column, an identification number column, and a feature amount parameter column. The feature amount classification includes [distance], [velocity], [acceleration], [tap interval], [phase difference], and [marker following]. For example, the feature amount [distance] has a plurality of feature amount parameters identified by identification numbers (1) to (7). Units are illustrated in parentheses [ ] of the feature parameters.

(1) A "maximum amplitude of the distance" [mm] is the difference between the maximum value and the minimum value of the amplitude in the waveform of the distance ((a) of FIG. 8). (2) A "total movement distance" [mm] is the total sum of the absolute values of the amounts of change in the distance during the entire measurement time of one measurement operation. (3) "Average of the local maximum points of the distance" [mm] is the average value of the values of the local maximum points of the amplitude in each cycle. (4) A "standard deviation of the maximum point of the distance" [mm] is the standard deviation of the above-mentioned value.

(5) A "slope (attenuation rate) of an approximate curve at the local maximum point of the distance" [mm/sec] is the slope of a curve approximating the local maximum point of the amplitude. This parameter mainly indicates a change in the amplitude due to fatigue during the measurement time. (6) A "variation coefficient of the local maximum point of the distance" is a variation coefficient of the local maximum point of the amplitude and the unit of the variation coefficient is a dimensionless quantity (represented by [-]). This parameter is a value obtained by normalizing the standard deviation with an average value. Therefore, it is possible to exclude an individual difference in the length of the finger. (7) A "standard deviation of a local maximum point of the distance" [mm] is the standard deviation of three adjacent local maximum points of the amplitude. This parameter is a parameter for evaluating the degree of local variation in amplitude in a short time.

Hereinafter, each feature amount parameter (not illustrated) will be described. The feature amount [velocity] has feature amount parameters indicated by the following identification numbers (8) to (22). (8) A "maximum amplitude of the velocity" [m/sec] is the difference between the maximum value and the minimum value of the velocity in the waveform of the velocity ((b) of FIG. 8). (9) "Average of the local maximum points of an opening velocity" [m/s] is an average value related to the maximum value of the velocity at the time of an opening operation in each finger tap waveform. The opening operation is an operation of changing two fingers from a closed state to a maximum open state ((d) in FIG. 8). (10) "Average of the local maximum points of a closing velocity" [m/sec] is an average value related to the local maximum value of the velocity at the time of a closing operation. The closing operation is an operation of changing two fingers from the maximum open state to the closed state. (11) A "standard deviation of the local maximum points of the opening velocity" [m/sec] is a standard deviation related to the maximum value of the velocity at the time of the opening operation. (12) "Average of the local maximum points of the closing velocity" [m/sec] is a standard deviation related to the local maximum value of the velocity at the time of the closing operation.

(13) An "energy balance" [-] is the ratio of the sum of squares of the velocity during the opening operation to the sum of squares of the velocity during the closing operation. (14) "Total energy" [$m^2/sec^2$] is the sum of squares of the velocity for the entire measurement time. (15) A "variation coefficient of the local maximum point of the opening velocity" [-] is a variation coefficient relating to the maximum value of the velocity at the time of the opening operation and is a value obtained by normalizing the standard deviation with an average value. (16) "Average of the local maximum points of the closing velocity" [m/sec] is a variation coefficient related to the minimum value of the velocity at the time of the closing operation.

(17) The "number of shakes" [-] is a value obtained by subtracting the number of large opening and closing finger taps from the number of reciprocating movements in which the sign of the waveform of the velocity changes. (18) "Average of a distance ratio at the peak of the opening velocity" [-] is the average value of a distance ratio at the maximum value of the velocity during the opening operation in a case in which the finger tap amplitude is 1.0. (19) "Average of a distance ratio at the peak of the closing velocity" [-] is the average value of the distance ratio at the maximum value of the velocity during the closing operation in a case in which the finger tap amplitude is 1.0. (20) A "ratio of the distance ratios at the peak of the velocity" [−] is the ratio of the value of (18) to the value of (19). (21) A "standard deviation of the distance ratio at the peak of the opening velocity" [−] is a standard deviation related to the distance ratio at the maximum value of the velocity during the opening operation in a case in which the finger tap amplitude is 1.0. (22) A "standard deviation of the distance ratio at the peak of the closing velocity" [−] is a standard deviation related to the distance ratio at the minimum value of the velocity during the closing operation in a case in which the finger tap amplitude is 1.0.

The feature amount [acceleration] has feature amount parameters indicated by the following identification numbers (23) to (32). (23) A "maximum amplitude of acceleration" [m/sec$^2$] is the difference between the maximum value and the minimum value of the acceleration in the waveform of the acceleration ((c) in FIG. 8). (24) "Average of the local maximum points of opening acceleration" [m/sec$^2$] is the average of the maximum values of the acceleration during the opening operation and is a first value among four types of extreme values that appear in one cycle of the finger tap. (25) "Average of the local minimum points of opening acceleration" [m/sec$^2$] is the average of the local minimum values of the acceleration during the opening operation and is a second value among the four types of extreme values. (26) "Average of the local maximum points of closing acceleration" [m/sec$^2$] is the average of the local maximum values of the acceleration during the closing operation and is a third value among the four types of extreme values. (27) "Average of the local minimum points of the closing acceleration" [m/sec$^2$] is the average of the local minimum values of the acceleration during the closing operation and is a fourth value among the four types of extreme values.

(28) "Average of contact time" [sec] is the average value of the contact time in the closed state of two fingers. (29) A "standard deviation of the contact time" [sec] is the standard deviation of the contact time. (30) A "variation coefficient of the contact time" [−] is a variation coefficient of the contact time. (31) The "number of zero crossings of acceleration" [−] is the average number of times the sign of acceleration changes in one cycle of the finger tap. This value is ideally two. (32) The "number of times movement is frozen" [−] is a value obtained by subtracting the number of large opening and closing finger taps from the number of reciprocating movements in which the sign of acceleration changes in one cycle of the finger tap.

The feature amount [tap interval] has feature amount parameters indicated by the following identification numbers (33) to (41). (33) The "number of taps" [−] is the number of finger taps for the entire measurement time in one measurement operation. (34) An "average tap interval" [sec] is an average value of the above-mentioned tap interval ((d) in FIG. 8) in the waveform of the distance. (35) A "tap frequency" [Hz] is the frequency at which a spectrum is the maximum in a case in which Fourier transform is performed for the waveform of the distance. (36) A "tap interval standard deviation" [sec] is a standard deviation related to the tap interval.

(37) A "tap interval variation coefficient" [−] is a variation coefficient related to the tap interval and is a value obtained by normalizing the standard deviation with an average value. (38) A "tap interval variation" [mm$^2$] is an integrated value at which the frequency is in the range of 0.2 to 2.0 Hz in a case in which spectrum analysis is performed for the tap interval. (39) "Skewness of a tap interval distribution" [−] is the skewness in the frequency distribution of the tap interval and indicates the degree of distortion of the frequency distribution from the normal distribution. (40) A "standard deviation of a local tap interval" [sec] is the standard deviation of three adjacent tap intervals. (41) A "slope (attenuation rate) of an approximate curve of the tap interval" [−] is the slope of a curve approximating the tap interval. This slope mainly indicates a change in the tap interval due to fatigue for the measurement time.

The feature amount [phase difference] has feature amount parameters indicated by the following identification numbers (42) to (45). (42) "Average of a phase difference" [deg] is the average value of a phase difference in the waveform of both hands. The phase difference is an index value that indicates the deviation of a finger tap of the left hand from the right hand as an angle in a case in which one cycle of the finger tap of the right hand is set to 360 degrees. In a case in which there is no deviation, the phase difference is 0 degrees. As the value of (42) or (43) becomes larger, the deviation of both hands becomes larger and more unstable. (43) A "standard deviation of the phase difference" [deg] is a standard deviation related to the phase difference. (44) "Similarity between both hands" [−] is a value indicating correlation when the time lag is 0 in a case in which a cross-correlation function is applied to the waveforms of the left and right hands. (45) A "time lag at which the similarity between both hands is the maximum" [sec] is a value indicating the time lag at which the correlation of (44) is the maximum.

The feature amount [marker following] has feature amount parameters indicated by the following identification numbers (46) to (47). (46) "Average of delay time from a marker" [sec] is an average value related to the delay time of the finger tap with respect to the time indicated by a periodic marker. The marker corresponds to stimulation, such as visual stimulation, auditory stimulation, or tactile stimulation. This parameter value is based on the time when two fingers are in a closed state. (47) A "standard deviation of the delay time from the marker" [sec] is a standard deviation related to the delay time.

[Detection of Abnormal Data without Using DB]

The non-DB-using abnormal data detection unit 14A performed by the abnormal data detection unit 14 of the abnormal data processing system 1 will be described. The non-DB-using abnormal data detection unit 14A determines whether or not there is an abnormality only from the measurement data without referring to the individual-subject DB 45A and the multiple-subject DB 45B. Specifically, the following abnormality detection items are exemplified. The abnormal data detection unit 14 detects the acquired data as abnormal data in a case in which there is a mismatch between the original characteristics of data and the characteristics of the acquired data. The acquired measurement data or the above-described various feature amounts obtained from the measurement data can be used for the detection. The abnormal data detection unit 14 that has detected abnormal data corresponding to the abnormal detection item performs a process corresponding to the detected abnormal data.

FIG. 10 illustrates an example of a signal waveform obtained when abnormal data is detected.

(E1) in Case in which User Continuously Measures Same Task by Mistake

In a case in which a plurality of data items corresponding to the same task are input, the data is detected as abnormal data. As a corresponding process, the user is asked whether of the first and second data items is used on the screen of the terminal device 4 and selects data. Alternatively, considering that the practice effect is obtained from the second measurement due to repetitive measurement, it may be determined that the first measurement that does not include the practice effect is always used. In addition, considering that the first measurement is likely to fail because the user is unfamiliar with measurement, it may be determined that the second measurement is always used. Further, the better of the first measurement and the second measurement may be used with reference to the feature amounts stored in the analysis evaluation data 43.

(E2) in Case in which Two-Handed Finger Tap is Selected by Mistake when One-Handed Finger Tap is Measured This is a case in which the user performs movement with the intention of measuring a one-handed finger tap, but, in practice, a two-handed finger tap is selected and measurement data is recorded on the system. For the measurement data of each hand, the time for which no movement is performed (hereinafter, referred to as a "movement non-execution time") is calculated. The movement non-execution time is obtained by using the above-mentioned feature amounts. For example, a time period for which (2) the "total movement distance" per unit time is equal to or less than a predetermined value TDc is defined. In addition to this definition, (14) the "total energy" or (33) the "number of taps" may be equal to or less than a predetermined value. In a case in which the movement non-execution time is equal to or greater than a predetermined value Tc for only one hand, it is erroneously determined that a task is performed with only one hand even though the task has been performed with both hands and the data is detected as abnormal data. For example, Tc can be predetermined to be two-thirds of the measurement time. In this case, assuming that the measurement time is 15 seconds, abnormal data is detected when the movement non-execution time is 10 seconds or more. As such, when the abnormal data is detected, the data of the hand corresponding to the movement non-execution time is ignored and the abnormal data is treated as the measurement data of a one-handed task including the data of only the other hand. In addition, the system may ask the user or the administrator whether to process the data on the screen of the terminal device 4 for confirmation, without automatically processing the data.

(E3) in Case in which One-Handed Finger Tap is Selected by Mistake when Two-Handed Finger Tap is Measured This is a case in which the user performs movement with the intention of measuring a two-handed finger tap, but, in practice, a one-handed finger tap is selected and measurement data is recorded on the system. As will be described below, on a task measurement screen illustrated FIG. 12, in a case in which a one-handed finger tap is performed, only the waveform of one hand is presented to the user. However, since the measurement device 3 has acquired the measurement data of both hands, the measurement data of both hands is stored in the background. The movement non-execution time is calculated for each hand in the measurement data of both hands as described in the previous item. In a case in which the movement non-execution time for both hands is less than the predetermined value Tc, it can be determined that the user has performed the two-handed task. Then, data including the data of the hand that has not been presented to the user is treated as the measurement data of the two-handed task. In addition, the system may ask the user or the administrator whether to process the data on the screen for confirmation, without automatically processing the data.

(E4) in Case in which Two-Handed Alternating Free-Run is Selected by Mistake at Time of Measurement of Two-Handed Simultaneous Free-Run This is a case in which the user performs movement with the intention of measuring two-handed simultaneous free-run, but the measurement system 2 instructs the user to perform two-handed alternating free-run. Among the feature amounts stored in the analysis evaluation data 43a, a feature amount for evaluating the cooperation of both hands is used in order to detect this abnormality. For example, (42) the "average of a phase difference" is 0° in an ideal two-handed simultaneous free-run in which the movement of both hands is completely simultaneous and is 180° in an ideal two-handed alternating free-run in which the movement of both hands is completely alternate. Therefore, in a case in which (42) the "average of a phase difference" is less than a predetermined value (for example, 90°), even though the two-handed alternating free-run is selected, the user can be regarded as performing movement with the intention of the two-handed simultaneous free-run. That is, it is considered that the two-handed alternating free-run has been selected by mistake at the time of the measurement of the two-handed simultaneous free-run, and the task data 42A is changed to the measurement data of the two-handed simultaneous free-run after the measurement. In this case, the system may ask the user whether to process the data on the screen for confirmation, without automatically processing the data. As an example in which other feature values are used, in a case in which (44) the "similarity between both hands" is equal to or greater than a predetermined value (for example, 0), the movement may be considered as the two-handed simultaneous free-run. In a case in which the absolute value of (45) the "time lag at which the similarity between both hands is the maximum" is less than a predetermined value (for example, (34) the "average tap interval"×0.25), the movement may be considered as the two-handed simultaneous free-run. In some cases, although the user intends to perform the two-handed simultaneous free-run, the user is not able to move both hands at the same time and measurement data close to the two-handed alternating free-run is obtained. In this case, the system may ask the user or the administrator whether to process the data on the screen for confirmation, without automatically processing the data as abnormal data.

(E5) in Case in which Two-Handed Simultaneous Free-Run is Selected by Mistake at Time of Measurement of Two-Handed Alternating Free-Run This is a case in which the user performs movement with the intention of measuring two-handed alternating free-run, but the measurement system 2 instructs the user to perform two-handed simultaneous free-run, contrary to the previous paragraph. It is possible to perform determination on the basis of the feature amount of a finger tap, similarly to the previous paragraph. In a case in which (42) the "average of a phase difference" is equal to or greater than a predetermined value (for example, 90° which is an intermediate value between an ideal value of 0° in the two-handed simultaneous free-run and an ideal value of 180° in the two-handed alternating free-run), even though the two-handed simultaneous free-run is selected, the user is likely to perform movement with the intention of the two-handed alternating free-run. That is, it is considered that the two-handed simultaneous free-run has been selected by mistake at the time of the measurement of the two-handed alternating free-run, and the task data 42A is changed to the two-handed simultaneous free-run after the measurement. As an example in which other feature values are used, in a case in which (44) the "similarity between both hands" is less than a predetermined value (for example, 0), the movement may be considered as the two-handed simultaneous free-run. In a case in which (45) the "time lag at which the similarity between both hands is the maximum" is equal to or greater than a predetermined value (for example, (34) the "average tap interval"×0.25), the movement may be considered as the two-handed simultaneous free-run. In some cases, although the user intends to perform the two-handed alternating free-run, the user moves both hands at the same time and measurement data close to the two-handed simultaneous free-run is obtained. In this case, the system may ask the user or the administrator whether to process the data on the screen for confirmation, without automatically processing the data as abnormal data.

(E6) in Case in which Two Fingers are Crossed During Measurement

This is a case in which the distance between two fingers is an abnormal value due to the cross of the thumb and the index finger during the measurement of a finger tapping movement. In a case in which a magnetic sensor is used as the motion sensor 20, the distance between two fingers may be estimated to be a very large value for the time period for which two fingers are crossed due to the nature of the magnetic sensor, as illustrated in FIG. 10(a). A feature value representing the amplitude of the waveform among the feature amounts stored in the analysis evaluation data 43 is used in order to detect the abnormality. For example, (1) the "maximum amplitude of the distance" is greater than a predetermined value (for example, 20 cm greater than the distance between two fingers of many people) or the maximum value of the distance between two fingers which has been measured before measurement, it can be considered that the abnormality in which two fingers are crossed has occurred. In addition, a time period for which the feature amount is greater than the maximum value of the distance between two fingers in the measurement data 42B (raw waveform data) before the feature amounts are calculated can be extracted to specify the time period for which abnormality has occurred. Since the phenomenon that two fingers are crossed is also a part of the nature of the finger tapping movement, it may be better not to exclude the data without considering it as abnormal data. In this case, the system may ask the user or the administrator whether to process the data on the screen for confirmation, without automatically processing the data as abnormal data.

(E7) in Case in which Motion Sensor is Detached from Finger During Measurement

This is a case in which the distance between two fingers is an abnormal value due to the detachment of the motion sensor from the finger during measurement. When the motion sensor is detached, the distance between two fingers is estimated to be a very large value as illustrated in FIG. 10(b). As in the previous paragraph, in a case in which a feature amount representing the amplitude of the waveform, such as (1) the "maximum amplitude of the distance", is greater than a predetermined value or the maximum value of the distance between two fingers and is maintained until the end of measurement, it can be considered that the motion sensor has been detached from the finger. Whether or not this state is maintained until the end of the measurement can be determined by extracting the time period for which the feature amount is larger than the maximum value of the distance between two fingers in the measurement data, as in the previous paragraph. In addition, when it is determined that the motion sensor has been detached from the finger even though a predetermined measurement time has not elapsed, the system may immediately end the measurement in real time and prompt re-measurement.

(E8) in Case in which Movement is Started During Measurement Time

This is a case in which the user starts movement during the measurement time, without correctly understanding a signal to start measurement. As illustrated in FIG. 10(c), in a case in which there is a movement non-execution time at the beginning of the measurement, it can be determined that this abnormality has occurred. The determination of whether or not there is a movement non-execution time can be implemented by the above-described method. In addition, the measurement time may be divided into a predetermined number (for example, 5) of segments and the feature amount of a finger tap may be calculated in each segment. In a case in which the feature amount is compared between the segments and there is a segment in which the value of the feature amount is clearly different from that in other segments, it may be determined that this abnormality has occurred. For example, a measurement time of 15 seconds can be divided into five 3-second segments. When (33) the "number of taps" is calculated for each of the segments, it is assumed that values of 0, 5, 5, 5, and 4 are obtained as the values of the numbers of taps in order from the first segment. In this case, when the presence or absence of a segment that is separated by N standard deviations or more (for example, N=2) from the average value of five feature values in the direction in which the magnitude of the movement decreases is checked, the number of taps in the first segment is 0. In this way, it is also possible to determine whether or not there is a movement non-execution time.

(E9) in Case in which Movement is Ended During Measurement Time

This is a case in which the user ends movement by mistake before the end of measurement. As illustrated in FIG. 10(d), in a case in which there is a movement non-execution time at the end of measurement, it can be detected that this abnormality has occurred. The determination of whether or not there is a movement non-execution time can be implemented by the above-described method. In addition, as in the previous paragraph, the determination may be implemented by a method which divides the measurement time into N segments and calculates the movement non-execution time. Further, when it is determined that movement has ended during a predetermined measurement time even though the predetermined measurement time has not elapsed, the system may immediately end the measurement in real time and prompt re-measurement.

(E10) in Case in which Movement is Suspended During Measurement Time

This is a case in which movement is suspended due to, for example, the entanglement of cables during measurement. As illustrated in FIG. 10(e), in a case in which there is a movement non-execution time during measurement, it can be detected that this abnormality has occurred. The determination of whether or not there is a movement non-execution time can be implemented by the above-described method. In addition, as in the previous paragraph, the determination may be implemented by a method which divides the measurement time into N segments and calculates the movement non-execution time. Further, when it is determined that movement has been suspended during a predetermined measurement time even though the predetermined measurement time has not elapsed, the system may immediately end the measurement in real time and prompt re-measurement.

[Detection of Abnormal Data Using DB]

The DB-using abnormal data detection unit 14B performed by the abnormal data detection unit 14 of the abnormal data processing system 1 will be described. For example, in a case in which new data of the user X is acquired, the DB-using abnormal data detection unit 14B determines whether or not the new data is abnormal with reference to the individual-subject DB 45A and the multiple-subject DB 45B in which the past data of the user X has been stored. Specifically, the following abnormality detection items are exemplified.

(E11) in Case in which Nature of Movement is Changed by User's Intention

This is a case in which the user intentionally insincerely performs movement or misunderstands the instruction of a task, which results in a low movement performance. This can be detected in a case in which the degree of divergence of the performance from that stored in the past DB (individual-subject DB) of the user or the past DB of many subjects (multiple-subject DB) is large as a result of the comparison with the past DB. A method for calculating the degree of divergence will be described below.

(E12) in Case in which Nature of Movement is Changed by User's Physical Conditions This includes a case in which the performance of movement deteriorates due to the deterioration of a brain function or a movement function or extreme fatigue and a case in which the performance of movement is improved by the effects of medication and rehabilitation. These can be detected when the degree of divergence of the performance from that stored in the past DB (individual-subject DB) of the user is large as a result of the comparison with the past DB. A method for calculating the degree of divergence will be described below.

(E13) in Case in which Someone Impersonates User

This is a case in which someone impersonates the user to change the nature of movement. This can be detected when the degree of divergence of the nature of movement from that stored in the past DB (individual-subject DB) of the user is large as a result of the comparison with the past DB. A method for calculating the degree of divergence will be described below.

<<Calculation of Degree of Divergence>>

A method for calculating the degree of divergence will be described. The degree of divergence is calculated by the individual-subject DB divergence degree calculation unit 14Ba, the multiple-subject DB divergence degree calculation unit 14Bb, and the composite divergence degree calculation unit 14Bc.

First, a divergence degree calculation method common to the individual-subject DB divergence degree calculation unit 14Ba and the multiple-subject DB divergence degree calculation unit 14Bb will be described. N (N 1) feature amounts of the finger tapping movement are selected and a data distribution in an N-dimensional space is generated for the DB (the individual-subject DB 45A or the multiple-subject DB 45B). It is assumed that the average of the data distribution is M $(=[m1, m2, \ldots, mN])$ and the standard deviation thereof is $\Sigma(=[\sigma1, \sigma2, \ldots, \sigma N])$. In addition, it is assumed that the data which is an abnormal data detection target is A $(=[a1, a2, \ldots, aN])$. In this case, the degree of divergence is calculated as $d=|(A-M)/\Sigma|$. Here, $\|$ indicates the absolute value of a vector (the square root of the sum of squares). When d is larger than a predetermined value dc, it is determined that the degree of divergence from the DB is sufficiently large. For example, when dc=1 is established, it can be said that the measurement data is out of 68.3% of the data close to the average in the DB. Similarly, when dc=2 is established, it can be said that the measurement data is out of 95.5% of the data. When dc=3 is established, it can be said that the measurement data is out of 99.7% of the data. That is, dc may be set to a small value in a case in which the user wants to strictly detect abnormal data and may be set to a large value in a case in which the user wants to roughly detect abnormal data. The degree of divergence may be defined by a method other than the above-described method and may be any index indicating divergence from the DB.

In the above-described calculation of the degree of divergence, the feature amounts of the finger tapping movement are used without any change. However, the feature amounts may be processed to create a new index. For example, principal component analysis may be applied to all of the feature amounts and N principal components having a high contribution rate may be used.

A change in the feature amounts of the finger tapping movement is observed to specify whether the performance of the movement has deteriorated or improved. For example, when (2) the "total movement distance", (14) the "total energy", or (33) the "number of taps" is less than the average of the individual-subject DB, it can be understood that the performance of the movement has deteriorated. Conversely, when these features are greater than the average of the individual-subject DB, it can be understood that the performance of movement has been improved.

In addition, in order to specify the cause of a change in the performance of the movement, a screen on which the user inputs, for example, whether or not the brain function or the movement function has deteriorated, whether or not the user feels fatigue, and whether or not the user receives a treatment, such as medication or rehabilitation before measurement may be provided. In this case, the input content may be referred to as the reason for abnormality detection (which will be described below in FIG. 15) when the performance of the movement has deteriorated or improved as compared to the individual-subject DB 45A. In this way, it is possible to increase the persuasiveness of the reason why the abnormal data is detected to the user.

<<Combination of Degree of Divergence>>

Figure 11:
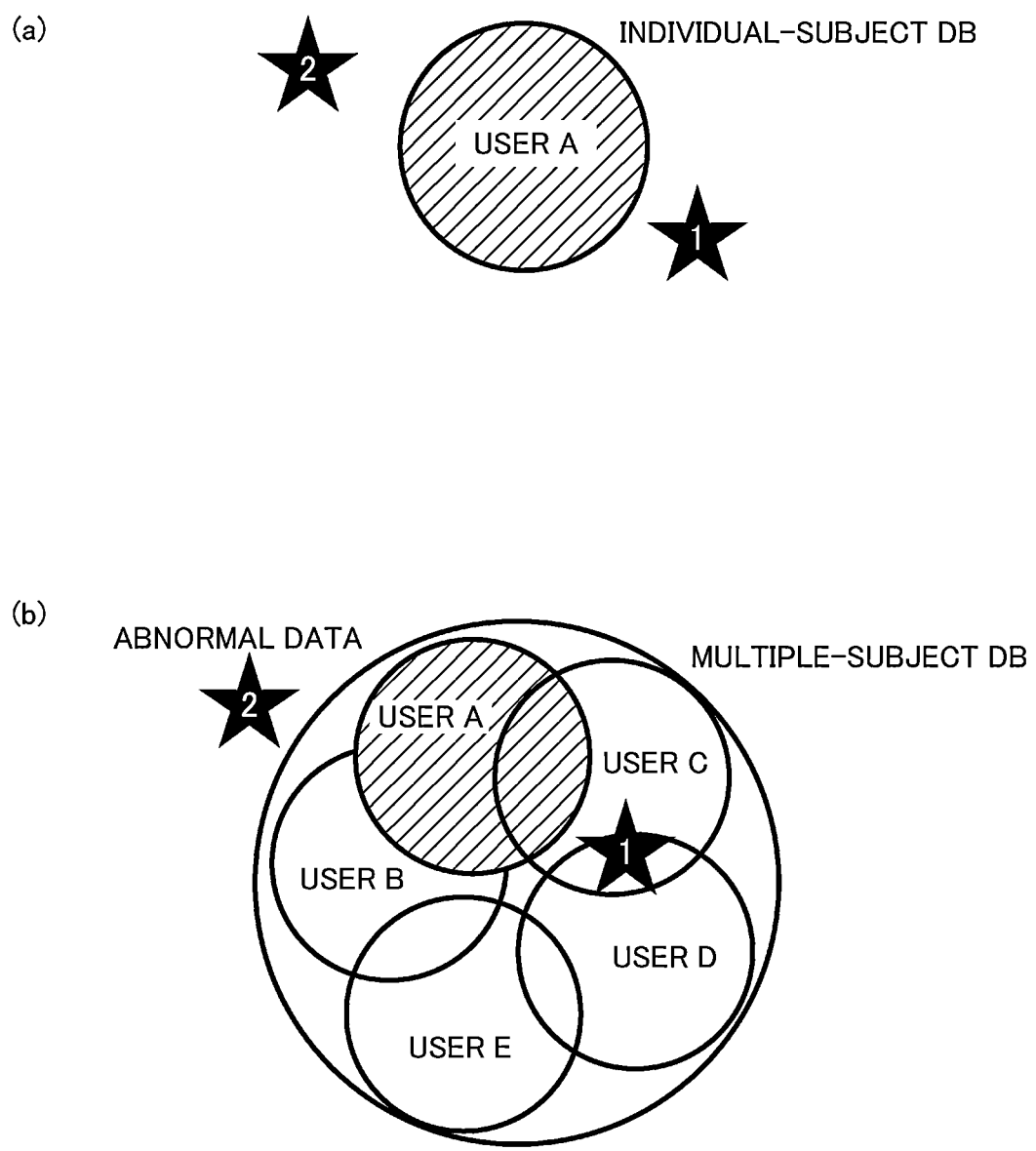
FIG. 11 is a conceptual diagram illustrating abnormal data detection using an individual-subject DB and abnormal data detection using a multiple-subject DB in Embodiment 1.

With the above-described method, the individual-subject DB divergence degree calculation unit 14Ba and the multiple-subject DB divergence degree calculation unit 14Bb can calculate the degree of divergence of the measurement data from the individual-subject DB 45A or the multiple-subject DB 45B. From this point of view, the individual-subject DB 45A makes it possible to detect abnormal data in which the characteristics of the data of the user have been reflected. Therefore, it is desirable to use the individual-subject DB 45A in order to accurately detect abnormal data. Specifically, as illustrated in FIG. 11(*a*), data 1 and data 2 represented by ★ have the same degree of divergence from the individual-subject DB 45A of a user A and are correctly detected as abnormal data. However, in a case in which the user has already performed measurement many times, the individual-subject DB 45A can be used. However, in a case in which the user has performed the measurement for the first time or only a small number of times, it is necessary to use the multiple-subject DB 45B since the individual-subject DB 45A has not been sufficiently accumulated. In FIGS. 11 to 13, a two-dimensional space formed by two feature amounts is considered and the DB and abnormal data are schematically illustrated. However, the number of feature amount may be one or three or more and a multidimensional space corresponding to the number of feature amounts used is considered.

In a case in which the multiple-subject DB 45B is used, there is an advantage that it is easy to prepare a DB since the data of users other than the user can be stored in advance. However, the multiple-subject DB 45B is an aggregate of the data of many users and the characteristics of the data of the users are not reflected in the multiple-subject DB 45B. Therefore, there is a disadvantage that the accuracy of detecting abnormal data is likely to be lower than that in a case in which the individual-subject DB 45A is used. Specifically, as illustrated in FIG. 11(b), data 1 and data 2 represented by ★ have different degrees of divergence from the multiple-subject DB 45B. There is a problem that the data 2 is correctly detected as abnormal data and the data 1 is not detected as abnormal data. From the awareness of the above-mentioned problem, it is considered that a technique which complements the advantages and disadvantages of the individual-subject DB 45A and the multiple-subject DB 45B and uses the two DBs together is needed.

Therefore, either the degree of divergence of the individual subject DB 45A or the degree of divergence of the multiple-subject DB 45B is not selected and used, but the degrees of divergence are combined to calculate a new degree of divergence (composite degree of divergence). It is considered that the use of the composite degree of divergence makes it possible to perform abnormal data detection in which the advantages and disadvantages when either the individual-subject DB 45A or the multiple-subject DB 45B is used are complemented.

The composite degree of divergence is calculated by the composite divergence degree calculation unit 14Bc. The composite degree of divergence ds is calculated using an individual-subject DB reliability coefficient c, an individual-subject DB divergence degree d1, and a multiple-subject DB divergence degree d2, as illustrated in FIG. 12(a). The individual-subject DB reliability coefficient c is an index indicating the degree of reliability of the individual-subject DB 45A and is a value of 0.0 to 1.0 as illustrated in FIG. 12(b). When the number of data items in the individual-subject DB 45A is 0, the individual-subject DB reliability coefficient c is 0.0 and gradually approaches 1.0 as the number of data items increases. An expression indicating the relationship between the individual-subject DB reliability coefficient c and the number of data items k may be any expression as long as the individual-subject DB reliability coefficient c increases as the number of data items increases. For example, as illustrated in FIG. 12(b), $c=1/(1+\exp(-\alpha(k-\beta)))+\gamma$ can be set by a sigmoid function (for example, $\alpha=0.1$, $\beta=50$). Here, when the individual-subject DB is trusted in a stage in which the number of data items is small, α may be set to a large value. When the individual-subject DB is trusted in a stage in which the number of data items is large, a may be set to a small value. In addition, β and γ may be adjusted such that c is 0 when k is 0. The composite degree of divergence ds is defined as $ds=d1\times c+d2\times(1.0-c)$ using the individual-subject DB reliability coefficient c defined as described above. When ds is larger than the predetermined value dc, it is determined that the degree of divergence from the DB is sufficiently large. That is, the individual-subject DB reliability coefficient c is a weight for the individual-subject DB divergence degree d1 and increases as the number of data items in the individual-subject DB 45A increases. A temporal attenuation divergence degree which will be described below may be used as the individual-subject DB divergence degree d1 and the multiple-subject DB divergence degree d2.

<<Calculation of Degree of Divergence Considering Time Series>>

A method for calculating the degree of divergence (hereinafter, referred to as a temporal attenuation divergence degree) calculated considering the time-series relationship of the data in the DB when the individual-subject DB divergence degree calculation unit 14Ba calculates the degree of divergence from the individual-subject DB 45A will be described. The data of the individual-subject DB 45A is accumulated over time by the periodical measurement of the user. However, the health conditions of the user change daily due to, for example, aging, a decline in cognitive functions, and a decline in movement functions. Therefore, when abnormal data is detected, it is considered that the more recent data has higher reliability and the older data has lower reliability. Specifically, as illustrated in FIG. 13(a), when the data in the individual-subject DB 45A changes over time in the order of 1→2→3, 4a and 4b have the same degree of divergence from the average of the DB. However, 4a needs to be determined as abnormal data since it is far from 3 which is the latest data and 4b does not need to be determined as abnormal data since it is close to 3 which is the latest data.

Therefore, as illustrated in FIG. 13(b), a temporal attenuation divergence degree calculated by increasing a weight for the most recent data and decreasing a weight for the older data is used as the individual-subject DB divergence degree d1. Specifically, the data in the individual-subject DB 45A is defined as Bi (=[bi1, bi2, ..., biN], i=1 to k (the number of data items in the individual-subject DB 45A)) and past data reliability $qi=p^n$ is defined according to the time ti going back from the acquisition of new data (0.0<p<1.0). Then, the average of the data distribution in the individual-subject DB 45A is defined as $M=q1B1+q2B2+ \ldots +qkBk$. When M is defined in this way, the more recent data has higher reliability and the older data has low reliability. Furthermore, the standard deviation Σ of the data distribution in the DB can be defined as $\Sigma=((q1B1-M)^2+(q2B2-M)^2+ \ldots +(qkBk-M)^2)/k$ using M. As described above, the individual-subject DB divergence degree d1 is calculated as $d=|(A-M)/\Sigma|$ using M and Σ.

The degree of divergence considering the time series has been described in consideration of the individual-subject DB 45A. However, the same calculation as described above can be performed in the multiple-subject DB 45B. That is, the multiple-subject DB divergence degree d2 may be calculated by calculating the degree of divergence considering the time series for each individual subject in the multiple-subject DB 45B and calculating the average of the degrees of divergence.

[Determination of Abnormal Data Processing]

The abnormal data processing determination unit 15 processes the abnormal data detected by the non-DB-using abnormal data detection unit 14A and the DB-using abnormal data detection unit 14B of the abnormal data processing system 1. Abnormal items of the non-DB-using abnormal data detection unit 14A and the DB-using abnormal data detection unit 14B performed by the abnormal data detection unit 14 of the abnormal data processing system 1 are stored in a table format in the abnormality detection reason-processing correspondence table 50B in the management table 50 illustrated in FIG. 14. This may be given in advance when the abnormal data processing system 1 is constructed or may be set by the administrator of the abnormal data processing system 1. A plurality of processes are described in a process column. In practice, one of the processes is selected and set. The abnormal data processing determination unit 15 performs a process corresponding to the abnormality detection item detected by the non-DB-using abnormal data detection unit 14A and the DB-using abnormal data detection unit 14B on the basis of the abnormality detection reason-processing correspondence table 50B.

[Execution of Abnormal Data Processing]

The abnormal data processing execution unit 16 executes the abnormal data processing content 46 determined by the abnormal data processing determination unit 15. In a case in which the measurement data is not used, it is assumed that the data is not registered in the individual-subject DB 45A and the multiple-subject DB 45B. In a case in which re-measurement is performed, the abnormal data processing content 46 of re-measurement is transmitted to the terminal device 4 through the communication unit 105. The terminal device 4 receives the abnormal data processing content 46 and performs re-measurement in cooperation with the measurement device 3. In a case in which the system inquires the user of data handling, the system transmits the content of the inquiry to the terminal device 4 through the communication unit 105. The terminal device 4 displays the content of the inquiry on the screen and the user sees the screen and responds to the inquiry. The content of the user's response is transmitted to the abnormal data processing system through the communication unit 105. The abnormal data processing execution unit 16 executes a process on the basis of the content of the user's response.

[Display Screen (1)—Menu]

Figure 15:
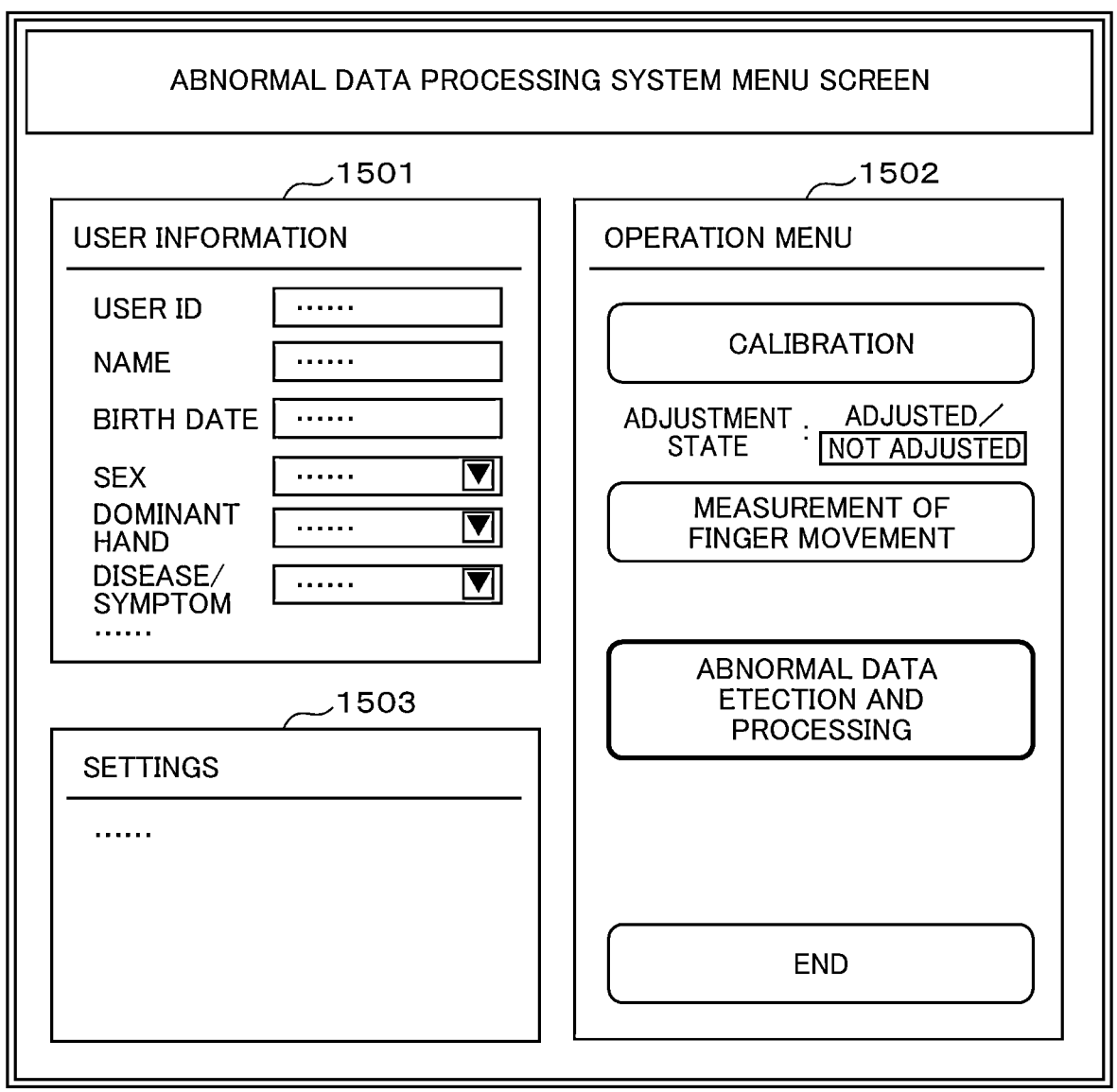
FIG. 15 is a plan view illustrating a menu screen as an example of a display screen in Embodiment 1.

FIG. 15 illustrates an example of a menu screen which is a service initial screen as an example of the display screen of the terminal device 4. The menu screen includes, for example, a user information column 1501, an operation menu column 1502, and a setting column 1503.

The user can input and register user information in the user information column 1501. In a case in which there is user information that has been input in, for example, an electronic medical record, the information may be associated with the user information. Examples of the user information that can be input include a user ID, a name, a birth date or age, sex, a dominant hand, a disease/symptom, and a memo. The dominant hand can be selected and input from, for example, the right hand, the left hand, both hands, and unknown. The disease/symptom may be selected and input from, for example, options in a list box or may be input in any text. For example, in a case in which this system is used in a hospital, not the user but the doctor may input the user information, instead of the user. The abnormal data processing system may be applied even in a case in which no user information is registered.

Operation items of the functions provided by the service are displayed in the operation menu column 1502. The operation items include, for example, "calibration", "measurement of finger movement", "abnormal data detection and processing", and "end". In a case in which the "calibration" is selected, a process related to the above-mentioned calibration, that is, the adjustment of, for example, the motion sensor 20 with respect to the user's finger is performed. In addition, the state of whether or not the adjustment has been performed is displayed. In a case in which the "measurement of finger movement" is selected, the screen is changed to a task measurement screen for measuring a finger movement task, such as a finger tap. In a case in which the "abnormal data detection and processing" is selected, abnormality is detected from the measurement data, the detection result of the abnormal data is displayed, and the screen is changed to a screen for processing the detected abnormal data. In a case in which the "end" is selected, this service is ended.

User setting can be performed in the setting column 1503. For example, in a case in which there is a type of abnormality detection item that the user, the measurer, or the administrator wants to detect, the user, the measurer, or the administrator can select the abnormality detection item from the options and can set the selected abnormality detection item. In addition, it is possible to select a process corresponding to each abnormality detection item. Further, it is possible to set an abnormal data detection threshold value. These settings are transmitted to the abnormal data processing system 1 through the communication unit 105 and the abnormal data processing system 1 detects and processes abnormal data with reference to the settings designated here.

[Display Screen (2)—Task Measurement]

Figure 16:
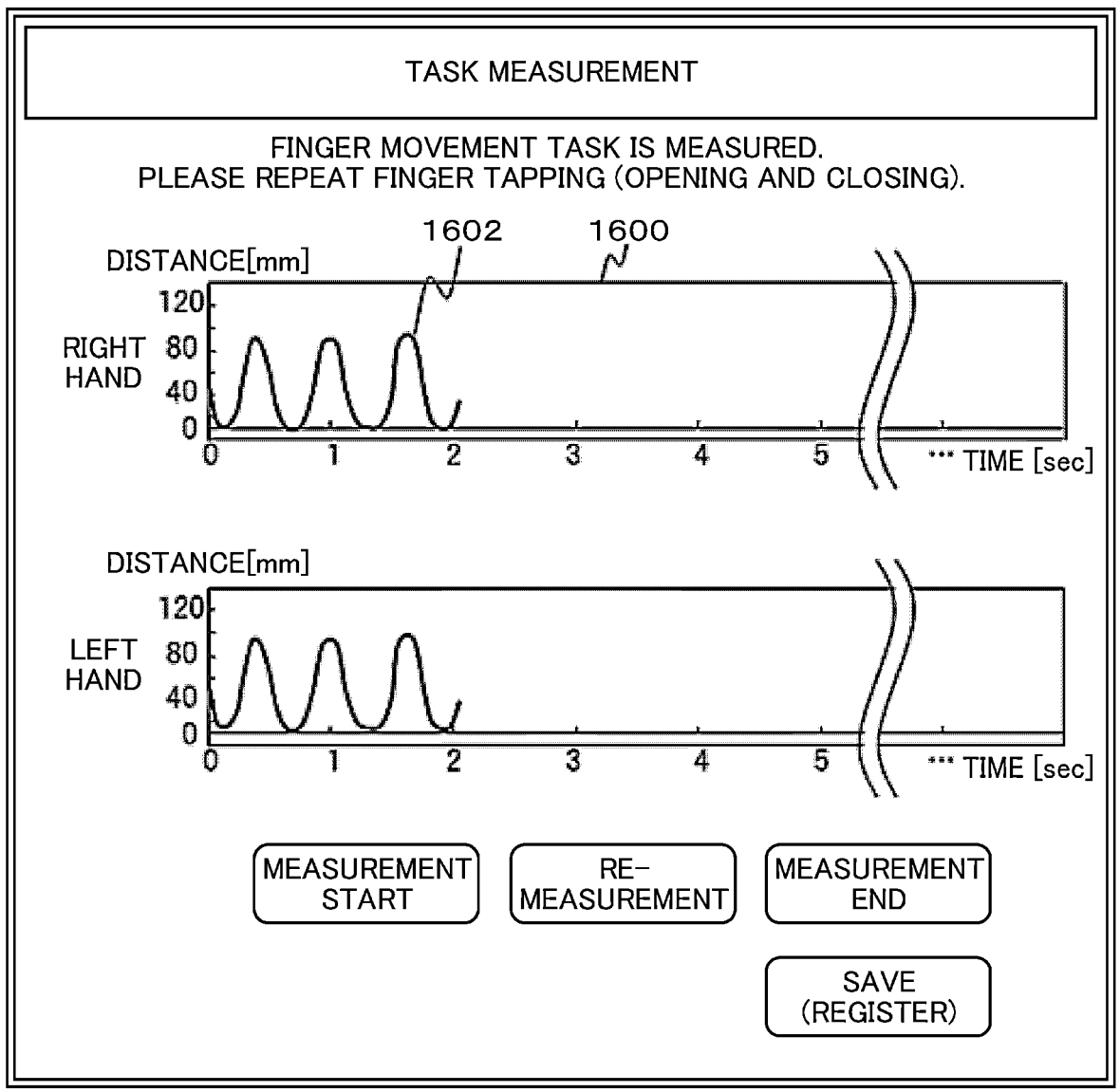
FIG. 16 is a plan view illustrating a task measurement screen as an example of the display screen in Embodiment 1.

FIG. 16 illustrates a task measurement screen as another example. Task information is displayed on this screen. For example, a graph 1600 in which the horizontal axis indicates time and the vertical axis indicates the distance between two fingers is displayed for each of the left and right hands.

Other teaching information for explaining the content of a task may be output to the screen. For example, a video region for explaining the content of the task with video and audio may be provided. The screen has operation buttons, such as "measurement start", "re-measurement", "measurement end", and "save (register)", which can be selected by the user. The user selects "measurement start" and performs task movement according to task information on the screen. The measurement device 3 measures the task movement to obtain a waveform signal. The terminal device 4 displays a measured waveform 1602 corresponding to the waveform signal under measurement on the graph 1600 in real time. After movement, the user selects "measurement end". When confirming the selection, the user selects "save (register)". The measurement device 3 transmits the measurement data to the abnormal data processing system 1.

[Display Screen (3)—Evaluation Result]

Figure 17:
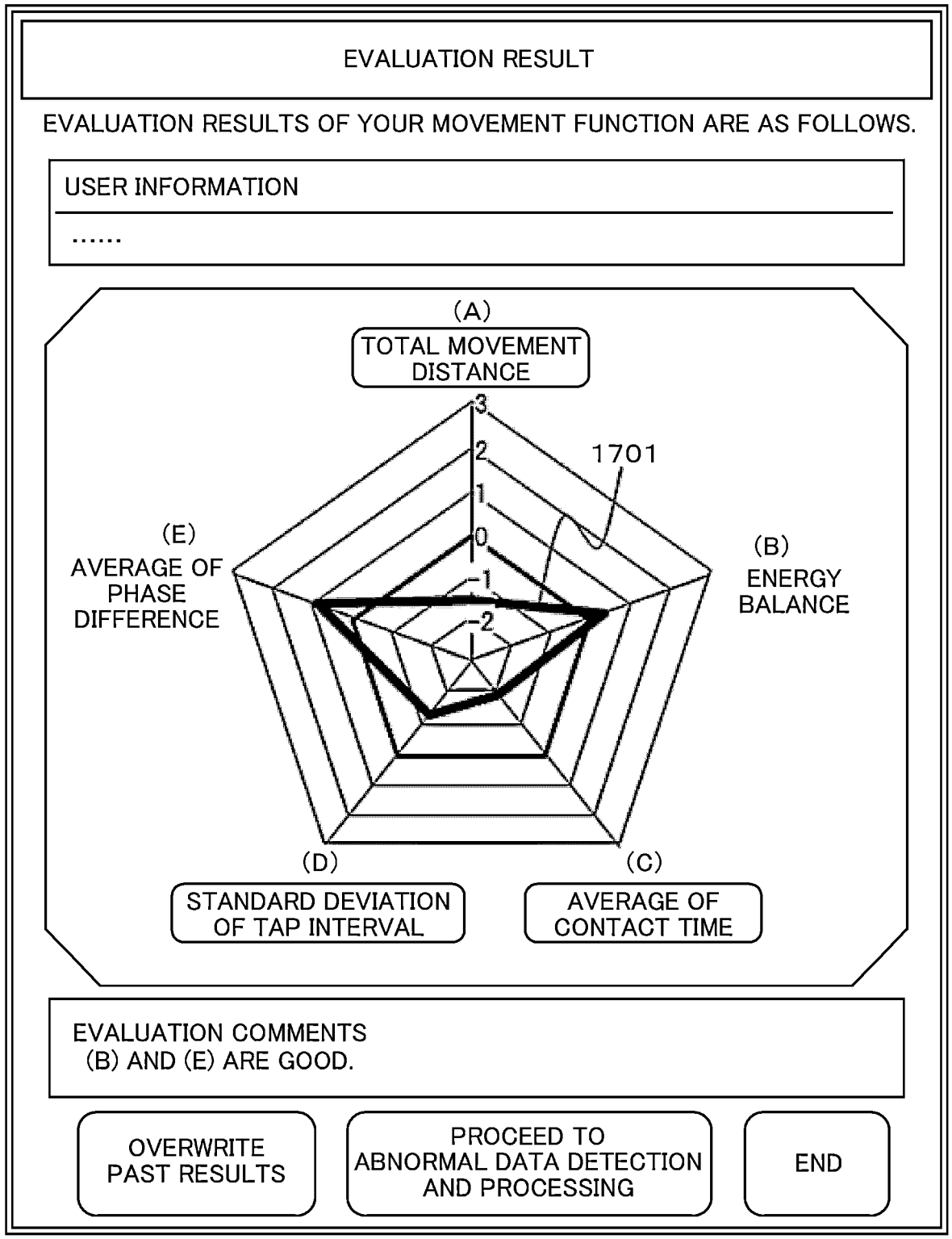
FIG. 17 is a plan view illustrating an evaluation result screen as an example of the display screen in Embodiment 1.

FIG. 17 illustrates an evaluation result screen as another example. Analysis evaluation result information of a task is displayed on this screen. After a task is analyzed and evaluated, this screen is automatically displayed. In this example, five feature amounts A to E of a finger tapping movement are displayed in a graph in a radar chart format. A solid frame 1701 indicates an analysis evaluation result after the current task measurement. A feature amount display method is not limited to the method of displaying the feature amounts in the radar chart and may be a method of displaying the feature amounts in a predetermined format such as a graph. The feature amount may be converted and displayed in a format such as a performance score (for example, a perfect score of 100). In addition to the graph of the feature amounts, for example, an evaluation comment related to the analysis evaluation result may be displayed. The analysis evaluation unit 13 creates an evaluation comment. For example, a message "(B) and (E) are good" is displayed. The screen has operation buttons such as "overwrite past results", "proceed to abnormal data detection and processing", and "end". The abnormal data processing system changes the screen to an abnormal data detection and processing screen in a case in which the "proceed to abnormal data detection and processing" is selected and changes the screen to the initial screen in a case in which the "end" is selected.

[Display Screen (3)—Abnormal Data Detection and Processing]

Figure 18:
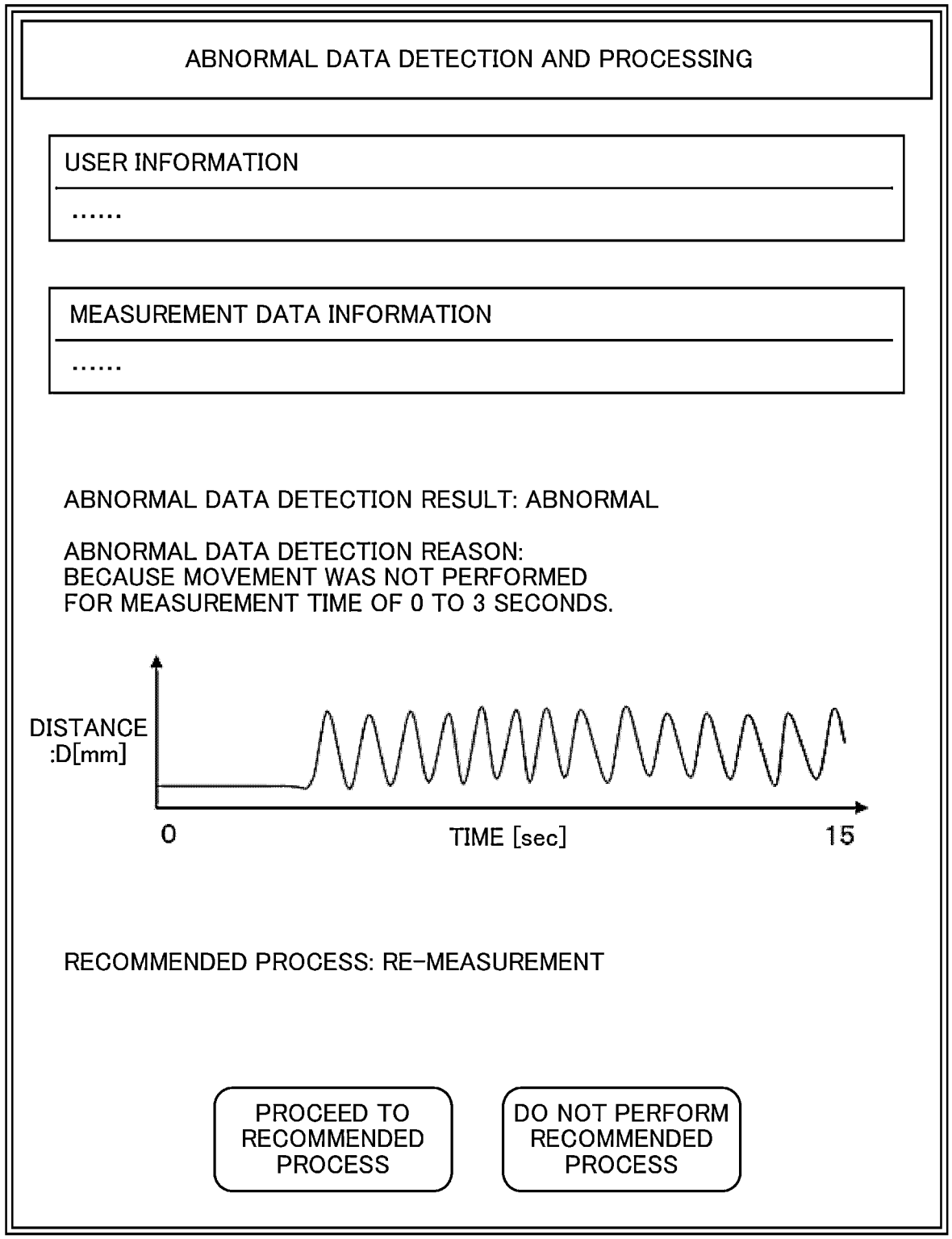
FIG. 18 is a plan view illustrating a first abnormal data detection and processing screen as an example of the display screen in Embodiment 1.

FIG. 18 illustrates an abnormal data detection and processing screen as another example. The abnormal data detection result 44 and the abnormal data processing content 46 transmitted from the abnormal data processing system 1 are displayed on this screen. This screen is displayed after the "abnormal data detection and processing" button illustrated in FIG. 11 or the "progress to abnormal data detection and processing" button illustrated in FIG. 18 is pressed. Basic information, such as user information or measurement data information, is displayed and then the detection result of abnormal data is displayed on this screen. In a case in which abnormality is detected in the measurement data, "abnormal" is displayed. In a case in which no abnormality is detected, "no abnormality" is displayed. Further, in a case in which measurement data is determined to be "abnormal", the reason for detecting the abnormal data is illustrated. The abnormal data detection reason is included in the abnormal data detection result 44 transmitted from the abnormal data processing system 1. In FIG. 18, a message "because movement was not performed in a measurement time of 0 to 3 seconds" is illustrated as an example of the non-DB-using abnormal data detection 14A. The waveform of the finger tapping movement is presented below the abnormal data detection reason to visually explain the abnormal data detection reason. In addition, a recommended process corresponding to the abnormal data detection reason is illustrated below the waveform. In FIG. 18, "re-measure" is given as an example of the corresponding process. A correspondence table between the abnormal data detection reason and the process is recorded on the abnormality detection reason-processing correspondence table 50B in the management table 50. The user, the measurer, or the administrator selects a "perform the recommended process" button when performing the recommended process illustrated in FIG. 18 and selects a "do not perform the recommended process" button when not wanting to perform the recommended process. In addition, the abnormal data processing system 1 may automatically perform the process and notify the result of the process after the process, without allowing the user, the measurer, or the administrator to select whether or not to perform the process.

Figure 19:
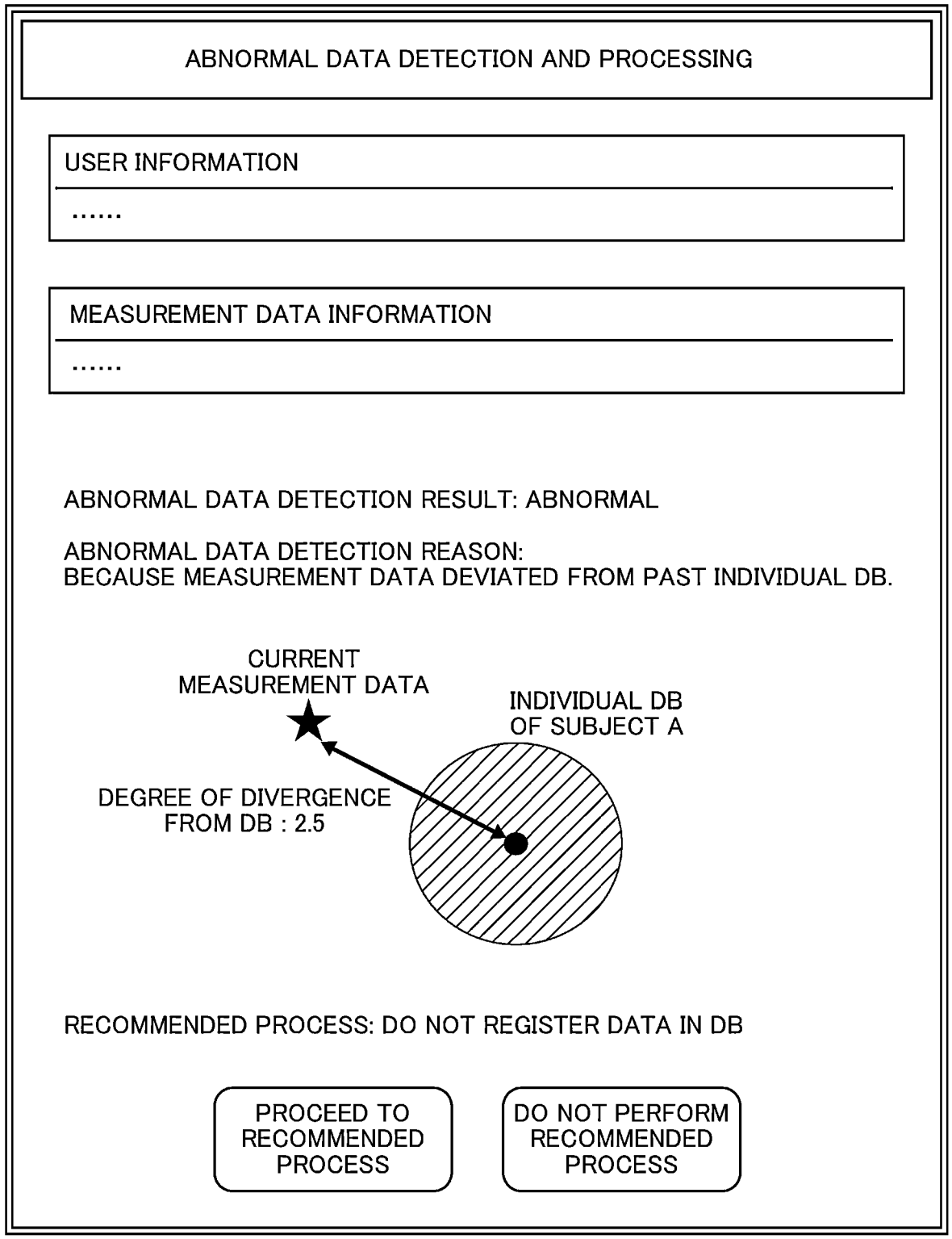
FIG. 19 is a plan view illustrating a second abnormal data detection and processing screen as an example of the display screen in Embodiment 1.

FIG. 19 illustrates another example of the abnormal data detection and processing screen. In FIG. 19, as an example of the DB-using abnormal data detection 14B, the abnormal data detection reason is "because the data has deviated from the past individual DB". "Do not register data in DB" is given as an example of the recommended process corresponding to the abnormal data detection reason.

[Effects]

According to the abnormal data processing system 1 of Embodiment 1, both the individual-subject DB 45A and the multiple-subject DB 45B are used to achieve highly accurate abnormal data processing. The reason is that a decrease in accuracy when the number of data items in the individual-subject DB 45A is insufficient can be covered by increasing a weight for the multiple-subject DB 45B and a decrease in accuracy due to incapability to reflect an individual differences when the multiple-subject DB 45B is used can be covered by increasing a weight for the individual-subject DB 45A.

Embodiment 2

An abnormal data processing system according to Embodiment 2 of the invention will be described with reference to FIGS. 20 to 26. The basic configuration of Embodiment 2 is the same as that of Embodiment 1. Hereinafter, portions of the configuration of Embodiment 2 which are different from those of the configuration of Embodiment 1 will be described.

[System (2)]

Figure 20:
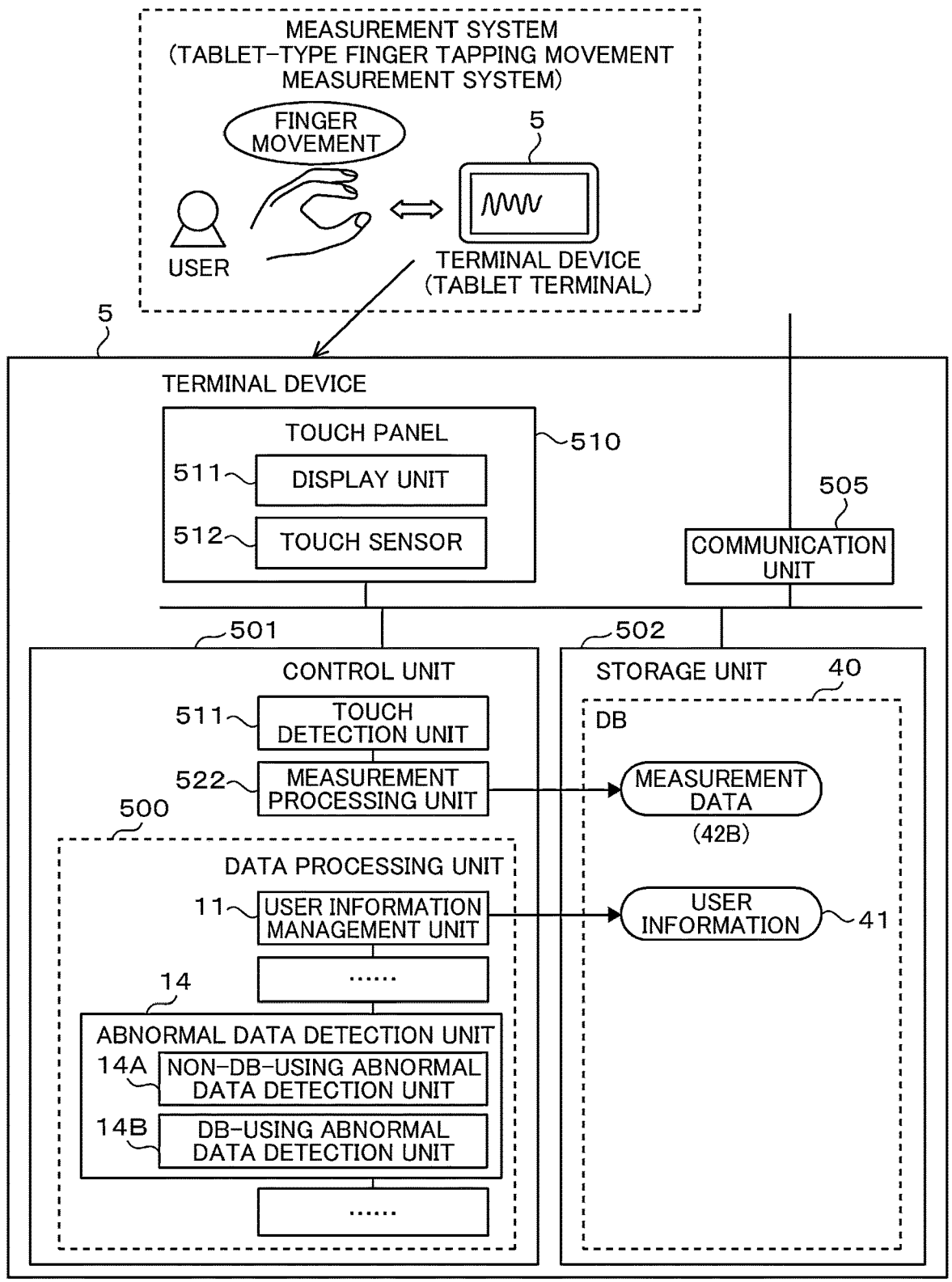
FIG. 20 is a block diagram illustrating the configuration of an abnormal data processing system according to Embodiment 2 of the invention.

FIG. 20 illustrates a human data measurement system including the abnormal data processing system according to Embodiment 2. The human data measurement system is provided in, for example, a hospital, a facility for the elderly, or the user's home. The human data measurement system according to Embodiment 2 The abnormal data processing system uses a measurement system which is a tablet-type finger tap movement measurement system. The measurement system includes a terminal device 5 which is a tablet terminal. In Embodiment 2, movement measurement and information display are performed using a touch panel provided in the terminal device 5. Embodiment 2 corresponds to an aspect in which the measurement function of the measurement device 3 and the display function of the terminal device 4 according to Embodiment 1 are integrated into one terminal device 5. The terminal device 5 may be a device that is installed in a facility or a device that is owned by the user.

The terminal device 5 includes, for example, a control unit 501, a storage unit 502, a communication unit 505, and a touch panel 510 which are connected to each other through a bus. The touch panel 510 includes a display unit 511 and a touch sensor 512. The display unit 511 is, for example, a liquid crystal display unit or an organic EL display unit and has a display screen. The touch sensor 512 is, for example, a capacitive type and is provided in a region corresponding to the display screen. The touch sensor 512 detects, as an electrical signal, a change in capacitance according to the approach or contact state of a finger on the display screen and outputs the detected signal to a touch detection unit 521.

The control unit 501 controls the entire terminal device 5, includes, for example, a CPU, a ROM, and a RAM, and implements a data processing unit 500 that performs abnormal data processing and the like, on the basis of software program processing. The configuration of the data processing unit 500 is substantially the same as that in Embodiment 1. The control unit 501 further includes the touch detection unit 521 and a measurement processing unit 522. The control unit 501 implements, for example, a function of obtaining measurement data through the touch panel 510, a function of processing and analyzing the measurement data, and a function of outputting information to a display screen of the display unit 511 of the touch panel 510. The touch detection unit 521 performs a process of detecting the approach or contact state of the user's finger and the movement state of the finger on the display screen as touch position coordinates and a time-series signal thereof on the basis of the detected signal from the touch sensor 512. The measurement processing unit 522 measures the position and movement of the finger on the display screen as a waveform signal and obtains measurement data, using the detected information of the touch detection unit 521. The measurement data corresponds to measurement data 42B. The data processing unit 500 performs abnormal data detection and abnormal data processing determination on the basis of the measurement data, using the same process as that in Embodiment 1, and displays the result of the process on the display screen of the display unit 511. In addition, for example, the data processing unit 500 creates analysis evaluation data and displays an evaluation screen on the display screen of the display unit 511. The data processing unit 500 has the same functions as the data processing unit illustrated in FIG. 2, such as a user information management unit 11 and an abnormal data detection unit 14 including a non-DB-using abnormal data detection unit 14A and a DB-using abnormal data detection unit 14B. The storage unit 502 has the same functions as the second storage unit 102 and stores, for example, user information 41, task data 42A, measurement data 42B, analysis evaluation data 43, an abnormal data detection result 44, an individual-subject DB 45A, a multiple-subjects DB 45B, a management table 50, and abnormal data processing content 46.

Example (1) of Movement and Display Screen

Figure 21:
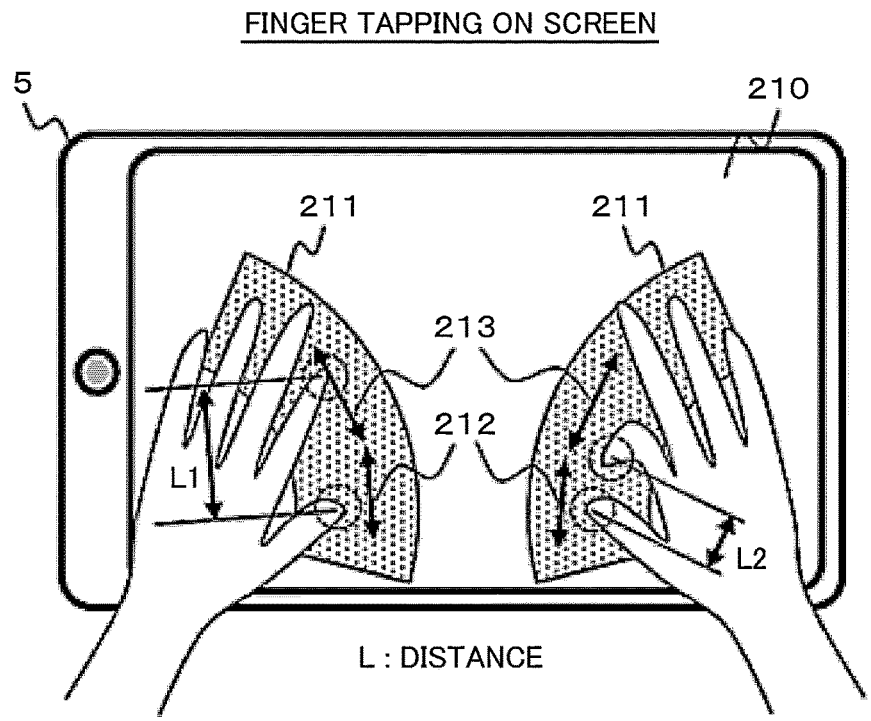
FIG. 21 is a plan view illustrating a finger tap on a screen as an example of movement in Embodiment 2.

FIG. 21 illustrates a method in which a finger tapping movement is performed on a display screen 210 of the terminal device 5. The terminal device 5 may provide a task using this method. In this method, the control unit 501 displays regions 211 in which two target fingers of both hands are placed on a background region of the display screen 210. In this case, the target two fingers are, for example, the thumb as a first finger and the index finger as a second finger. The user places the two fingers of each hand so as to come into contact with the region 211 or to be close to the region 211. In this example, when the fingers are moved, the state in which the finger touches the region 211 of the display screen is basically maintained, which depends on, for example, the touch sensor 512. The user performs a finger tap of opening and closing two fingers in the region 211. The terminal device 5 measures the finger tapping movement through, for example, the touch sensor 512 and obtains measurement data such as a waveform signal as in Embodiment 1. Arrows indicate the movement 212 of the first finger and the movement 213 of the second finger on the region 211. As a distance L between two fingertips, a distance L1 on the left hand side and a distance L2 on the right hand side are shown.

Figure 22:
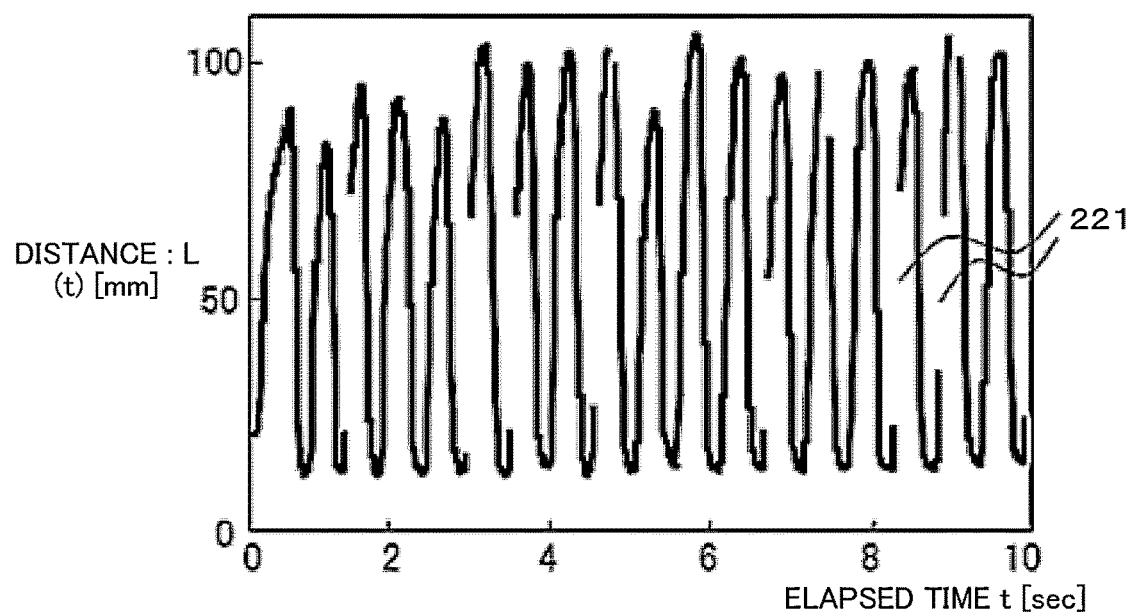
FIG. 22 is a waveform diagram illustrating the waveform of a distance between two fingers of the finger tap on the screen in Embodiment 2.

FIG. 22 illustrates a waveform signal of the distance L between two fingers as an example of the measurement data corresponding to the finger tapping movement illustrated in FIG. 21. The horizontal axis indicates the elapsed time t [sec] and the vertical axis indicates the distance L(t) [mm] for each elapsed time t. A waveform portion 221 indicates a state in which the finger is separated from the region 211 to some extent. In a case in which the waveform is broken in this way, a continuous waveform can be obtained by interpolating the waveform in a state in which the finger is on the region 211. The terminal device 5 extracts feature amounts on the basis of the measurement data, performs abnormal data detection, abnormal data processing determination, and abnormal data processing execution, and presents the results, using the method, as in Embodiment 1.

Example (2) of Movement and Display Screen

FIG. 23 illustrates a reaching method as another example of the finger tapping movement and the display screen. The terminal device 5 may provide a task using the reaching method. (a) of FIG. 23 illustrates cross leaching. First, a FIG. 231 of the initial position is displayed on the display screen 210 of the terminal device 5 and measurement is started in a state in which a target finger, for example, the index finger is placed on the FIG. 231 of the initial position. After the measurement is started, a target FIG. 232 corresponding to a marker, for example, a cross is displayed on the display screen 210. The control unit 501 displays the FIG. 232 at different positions, for example, at a predetermined cycle.

The user performs a finger tap so as to extend the fingers following the position of the FIG. 232. In this example, a state in which the user taps a position 233 that deviates from the center position of the FIG. 232 with the finger is shown. There is a distance E corresponding to the deviation between the center position of the target FIG. 232 and the tap or touch position 233. The terminal device 5 calculates, for example, the distance E or a delay time TD as one of the feature amounts on the basis of the measurement data. The delay time TD is a period from the time when the target FIG. 232 is displayed in a standby state in which the finger is placed on the FIG. 231 of the initial position to the time when the finger touches the target FIG. 232.

(b) of FIG. 23 illustrates circular reaching. A circular region is displayed as a target FIG. 234. Similarly, the user performs a finger tap on the circular region of the FIG. 234. As a feature amount, for example, the distance between the center position of the FIG. 234 and the tap position is extracted.

Example (3) of Movement and Display Screen

FIG. 24 illustrates a continuous touch method as another example of the finger tapping movement and the display screen. The terminal device 5 may provide a task or practice using the continuous touch method. FIG. 24(a) illustrates a one-handed continuous touch. A FIG. 241 for the touch of the thumb of the left hand, for example, a circular region is displayed at one position on the display screen 210, for example, in the vicinity of the lower left corner of the display screen 210. The user continuously touches the displayed FIG. 241 with a finger. In a case in which the FIG. 241 is not displayed, the user removes the finger from the FIG. 241. The control unit 501 controls the display of the FIG. 241. For example, the display and non-display of the FIG. 241 are switched at a predetermined cycle and the FIG. 241 is displayed a predetermined number of times. In addition to the display of the FIG. 241, for example, auditory stimulation may be given as teaching information. As feature amounts, for example, the number of touches, touch interval, and touch delay time of the FIG. 241 are extracted.

FIG. 24(b) illustrates a two-handed simultaneous continuous touch. Figures 242 indicating the touch positions of the target fingers of the left and right hands are displayed at two positions on the display screen 210. The user continuously touches the displayed figures 242 with both hands at the same timing. Similarly, a two-handed alternating continuous touch is possible. In this case, the control unit 501 performs switching such that the left and right figures 242 are alternately displayed. The user touches these figures 242 with the left and right hands at alternate timings. As a feature amount, for example, a phase difference between the touches of the left and right FIG. 242 is extracted.

As another example of the movement, for example, auditory stimulus may be output as the teaching information without displaying the figure. For example, two types of sounds may be output at a predetermined cycle at a touch time and a non-touch time.

Example (4) of Movement and Display Screen

FIG. 25 illustrates a tapping method according to light as another example of the finger tapping movement and the display screen. FIG. 25(a) illustrates a one-handed tap. A tapping FIG. 251 for the target finger of the left hand and a FIG. 252 serving as visual stimulation light for indicating the tapping timing of the FIG. 251 are displayed on the display screen 210. The control unit 501 blinks the FIG. 252 such that the display and non-display of the FIG. 252 are switched. The user taps the tapping FIG. 251 at the timing when the FIG. 252 is displayed. As another example of the movement, a sound for auditory stimulation may be output instead of the FIG. 252 for visual stimulation or a continuous touch method may be used. As a feature amount, for example, there is a time lag between the time when simulation is periodically generated and the tap or touch time. The time lag corresponds to a delay time from the time when the FIG. 252 is displayed to the time when the FIG. 251 is tapped. FIG. 25(b) similarly illustrates the case of a two-handed simultaneous tap. Two tapping figures 251 are provided on the left and right sides and two figures 252 for visual stimulation are displayed on the left and right sides so as to be blinked at the same timing. Similarly, in the case of a two-handed alternating tap, the control unit 501 displays the two figures 252 on the left and right sides so as to be blinked at alternate timings.

Example (5) of Movement and Display Screen

Figure 26:
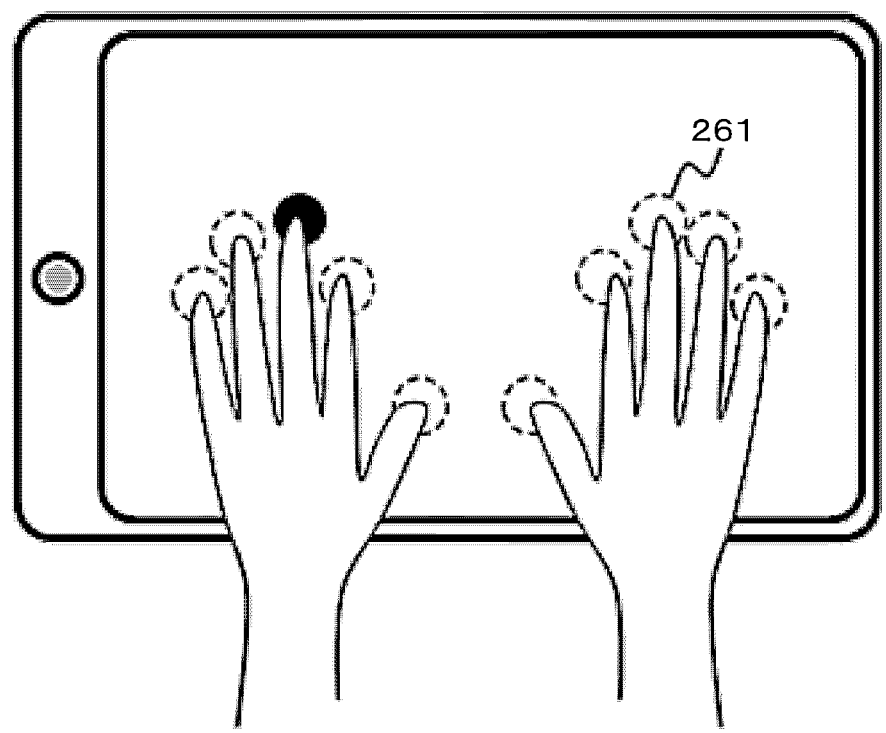
FIG. 26 is a plan view illustrating a five-finger tap as an example of the movement in Embodiment 2.

FIG. 26 illustrates a five-finger tapping method as another example of the finger tapping movement and the display screen. The terminal device 5 may provide a task using the five-finger tapping method. In this method, five fingers of the target hand are used. The terminal device 5 displays tapping figures 261 for five fingers of each of both hands, that is, a total of ten fingers on the background region of the display screen 210. First, the user places five fingers so as to touch the display screen 210. The terminal device 5 automatically adjusts and sets the display positions of the figures 261 on the basis of the detection of the touch positions. The terminal device 5 controls the display of the figures 261 at each position. The terminal device 5 changes the FIG. 261 at the position to be tapped to a specific display state (represented by, for example, a black circle) and changes the other figures 261 at the positions not to be tapped to another display state. The terminal device 5 controls the switching of the display state of the FIG. 261. The user taps the FIG. 261 with the finger according to the display of the FIG. 261 to be tapped.

[Feature Amounts]

Examples of the feature amounts unique to Embodiment 2 are as follows.

Feature amount parameters related to the reaching method are as follows. (2-1) An "average value of a delay time from target display" [sec] is an average value related to the delay time. (2-2) A "standard deviation of delay time from target display" [sec] is the standard deviation of the delay time. (2-3) An "average value of a position error with respect to a target" [mm] is the average value of the distance E. (2-4) A "standard deviation of a position error with respect to a target" [mm] is a standard deviation related to the distance E.

Feature amount parameters related to the one-handed continuous touch method are as follows: (2-5) the "number of taps" [–]; (2-6) a "tap interval average" [sec]; (2-7) a "tap frequency" [Hz]; (2-8) a "tap interval standard deviation [sec]; (2-9) a "tap interval variation coefficient" [–]; (2-10) a "tap interval variation" [$mm^2$]; (2-11) "skewness of a tap interval distribution" [–]; (2-12) a "standard deviation of a local tap interval" [sec]; and (2-13) a "tap interval attenuation rate". The definition of each feature amount is the same as that in Embodiment 1.

Feature amount parameters related to the two-handed continuous touch method are as follows. (2-14) "Average of a phase difference" [deg] is, for example, an average value of the phase difference of a two-handed touch. (2-15) A "standard deviation of a phase difference" [deg] is the standard deviation of the phase difference.

Feature amount parameters related to a touch or tapping method according to light or auditory stimulation. (2-16) An "average value of time lag with respect to stimulus" [sec] is the average value of the above-described time lag. (2-17) A "standard deviation of time lag with respect to stimulus" [deg] is the standard deviation of the above-described time lag.

[Detection of Abnormal Data without Using DB]

The non-DB-using abnormal data detection unit 14A performed by the abnormal data detection unit 14 of the data processing unit 500 will be described. Similarly to Embodiment 1, the non-DB-using abnormal data detection unit 14A determines whether or not there is an abnormality only from the measurement data without referring to the DB. Basically, the same abnormality detection items as those in Embodiment 1 are given as examples. However, only the items unique to this embodiment will be described below. Among the abnormality items described in Embodiment 1, (E2) does not occur in the case of a task using both hands in this embodiment since the positions touched with both hands are visually indicated. In addition, since (E6) is the phenomenon unique to the magnetic sensor, (E6) may not be considered in this embodiment in which the screen is touched.

(E4) in Case in which Two-Handed Alternating Tap is Selected by Mistake at Time of Measurement of Two-Handed Simultaneous Tap This is a case in which the user performs movement with the intention of measuring a two-handed simultaneous tap, but, in practice, a two-handed alternating tap is selected and measurement data is recorded on the system. Among the feature amounts stored in the analysis evaluation data 43, a feature amount for evaluating the cooperation of both hands is used in order to detect this abnormality. For example, (2-14) the "average of a phase difference" is 0° in an ideal two-handed simultaneous tap in which the movement of both hands is completely simultaneous and is 180° in an ideal two-handed alternating tap in which the movement of both hands is completely alternate. Therefore, in a case in which (2-14) the "average of a phase difference" is less than a predetermined value (for example, 90°), even though the two-handed alternating tap is selected, the user can be regarded as performing movement with the intention of the two-handed simultaneous tap. That is, it is considered that the two-handed alternating tap has been selected by mistake at the time of the measurement of the two-handed simultaneous tap, and the task data 42A is changed to the measurement data of the two-handed simultaneous tap after the measurement.

(E5) in Case in which Two-Handed Simultaneous Tap is Selected by Mistake at Time of Measurement of Two-Handed Alternating Tap This is a case in which the user performs movement with the intention of measuring a two-handed alternating tap, but, in practice, a two-handed simultaneous tap is selected and measurement data is recorded on the system, contrary to the previous paragraph. It is possible to perform determination on the basis of the feature amounts of a finger tap, similarly to the previous paragraph. For example, (2-14) the "average of a phase difference" is equal to or greater than a predetermined value (for example, 90°), even though the two-handed simultaneous tap is selected, the user is likely to perform movement with the intention of the two-handed alternating tap. That is, it is considered that the two-handed simultaneous tap has been selected by mistake at the time of the measurement of the two-handed alternating tap, and the task data 42A is changed to the measurement data of the two-handed simultaneous tap after the measurement.

(E7) in Case in which Finger Comes Off Predetermined Position During Measurement This is a case in which the finger touches a position that deviates from a predetermined position designated on the screen during measurement. It can be determined that this abnormality has occurred in a case in which there is a predetermined period of movement-non-execution time. Specifically, for example, the movement non-execution time can be evaluated as the time when (2-5) the "number of taps" is 0. In addition, even before a predetermined measurement time ends, measurement may be ended in real time and re-measurement may be prompted. Further, the measurement data may not be detected as abnormal data and a touch around the predetermined position may also be detected. Then, visual or audible guidance may be provided such that the user can return to a predetermined correct position in a case in which the touch position deviates from the predetermined position. The movement non-execution time in (E8), (E9), and (E10) may be evaluated as the time when (2-5) the "number of taps" is 0 as in this abnormality detection item.

[Effects]

According to the abnormal data processing system of Embodiment 2, both the individual-subject DB 45A and the multiple-subject DB 45B are used to achieve highly accurate abnormal data processing, similarly to Embodiment 1. In Embodiment 2, particularly, it is not necessary to provide, for example, the motion sensor 20. Therefore, it is possible to reduce the time and effort required for the user to perform measurement.

Embodiment 3

An abnormal data processing system according to Embodiment 3 of the invention will be described with reference to FIGS. 27 to 29. The basic configuration of Embodiment 3 is the same as that of Embodiment 1. Hereinafter, portions of the configuration of Embodiment 2 which are different from those of the configuration of Embodiment 1 will be described.

[System (3)]

Figure 27:
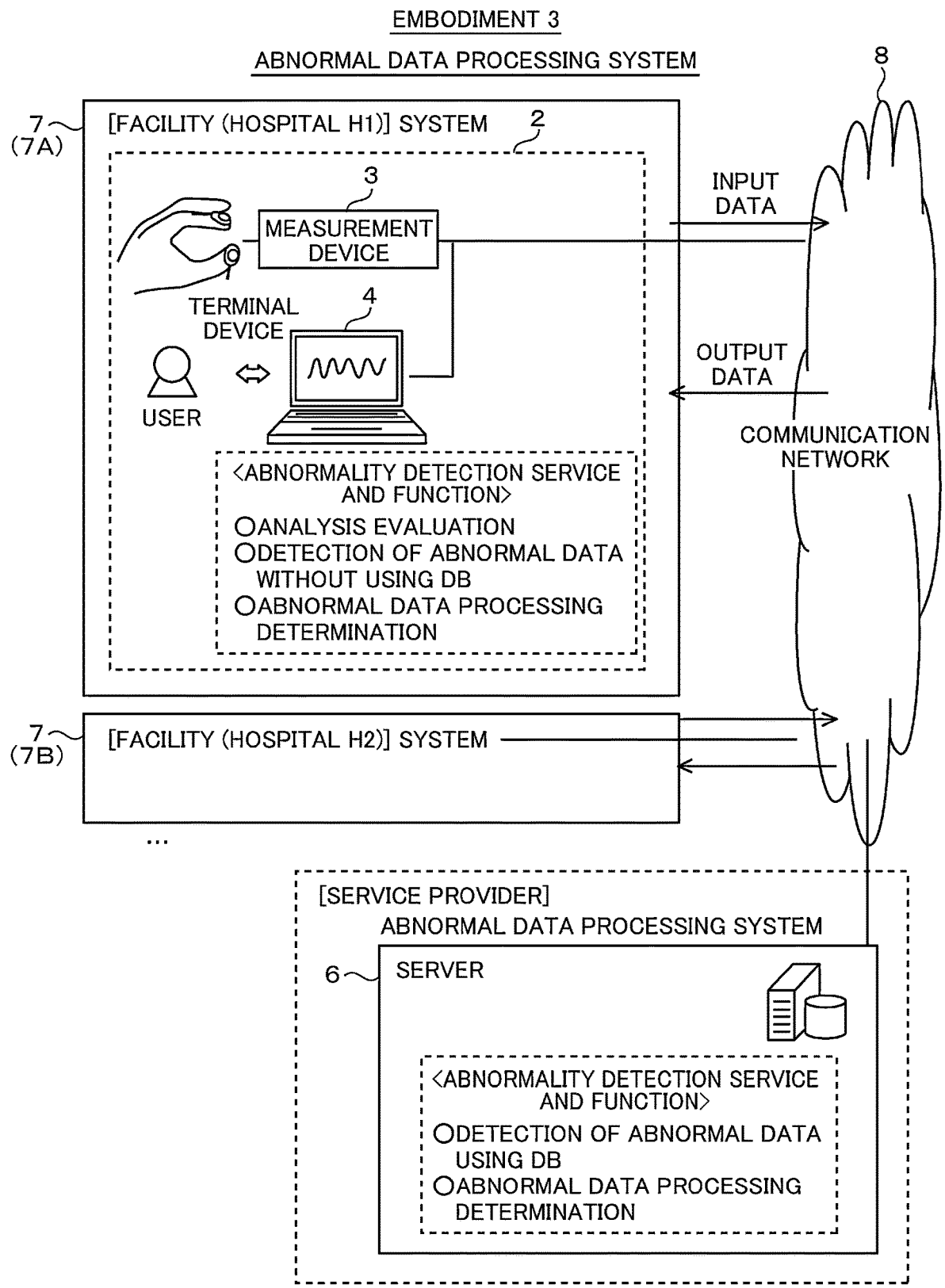
FIG. 27 is a block diagram illustrating the configuration of an abnormal data processing system according to Embodiment 3 of the invention.

FIG. 27 illustrates an abnormal data processing system according to Embodiment 3. The abnormal data processing system includes a server 6 of a service provider and systems 7 in a plurality of facilities, which are connected to each other through a communication network 8. The communication network 8 or the server 6 may include a cloud computing system. The functions of the abnormal data processing system according to Embodiment 3 are shared by the terminal devices 4 of the systems 7 and the server 6. The sharing will be described below.

The facilities can include various types of facilities, such as a hospital, a medical examination center, a public facility, an entertainment facility, and a user's home. The facility is provided with the system 7. Examples of the system 7 in the facility include a system 7A of a hospital H1 and a system 7B of a hospital H2. For example, each of the system 7A and the system 7B of the hospitals includes the measurement device 3 and the terminal device 4 forming the same measurement system 2 as that in Embodiment 1. The systems 7 may have the same configuration or may have different configurations. The system 7 of the facility may include, for example, a hospital electronic medical record management system. The measurement device of the system 7 may be a dedicated terminal.

The server 6 is a device under the control of the service provider. The server 6 has a function of providing the same abnormal data processing service as that in the abnormal data processing system 1 according to Embodiment 1 as an information processing service to the facilities and the users. The server 6 provides service processing to the measurement system using a client-server method. The server 6 has, for example, a user management function in addition to these functions. The user management function is a function of registering, accumulating, and managing, for example, the user information, measurement data, and analysis evaluation data, of user groups obtained through the systems 7 of a plurality of facilities in the DB. The terminal device 5 according to Embodiment 3 does not need have a function of processing abnormal data and has a measurement function using a touch panel and a display function of displaying, for example, the detection results of abnormal data generated by the server 6.

[Server]

Figure 28:
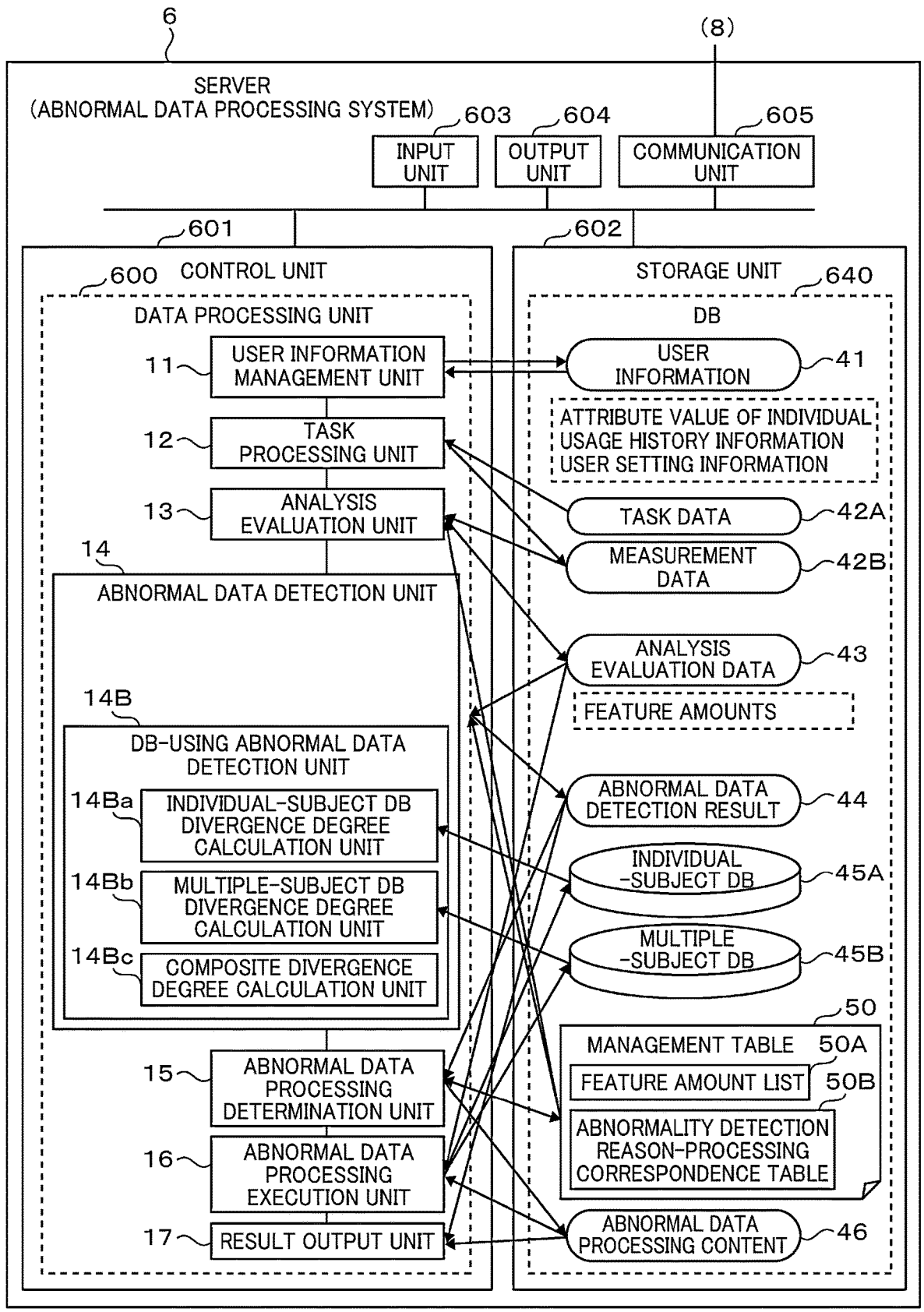
FIG. 28 is a block diagram illustrating the configuration of a server which is an abnormal data processing system according to Embodiment 3.

FIG. 28 illustrates the configuration of the server 6. The server 6 includes a control unit 601, a storage unit 602, an input unit 603, an output unit 604, and a communication unit 605 which are connected to each other through a bus. The input unit 603 is a portion that inputs an operation of, for example, the administrator of the server 6. The output unit 604 is a portion that displays a screen to, for example, the administrator of the server 6. The communication unit 605 has a communication interface and performs a communication process with the communication network 8. The storage unit 602 stores a DB 640. The DB 640 may be managed by, for example, a DB server other than the server 6.

The control unit 601 controls the entire server 6, includes, for example, a CPU, a ROM, and a RAM, and implements a data processing unit 600 that performs, for example, abnormal data detection and abnormal data processing determination on the basis of software program processing. The data processing unit 600 includes a user information management unit 11, a task processing unit 12, an analysis and evaluation unit 13, an abnormal data detection unit 14, an abnormal data processing determination unit 15, an abnormal data processing execution unit 16, and a result output unit 17. Unlike Embodiment 1, the abnormal data detection unit 14 does not include the non-DB-using abnormal data detection unit 14A and includes only the DB-using abnormal data detection unit 14B.

The user information management unit 11 registers user information related to a user group of the systems 7 in a plurality of facilities as user information 41 in the DB 640 and manages the user information. The user information 41 includes, for example, an attribute value, usage history information, and user setting information for each user. The usage history information includes information on the results of each user using the abnormal data processing service in the past.

[Server Management Information]

FIG. 29 illustrates an example of the data configuration of the user information 41 managed by the server 6 in the DB 640. A table of the user information 41 includes, for example, a user ID, a facility ID, an in-facility user ID, sex, age, a disease, a severity score, a symptom, history information. The user ID is unique identification information of the user in this system. The facility ID is identification information of the facility in which the system 7 is installed. In addition, for example, the communication address of the measurement device of each system 7 is managed. The in-facility user ID is user identification information in a case in which the user identification information managed in the facility or the system 7 is present. That is, the user ID and the in-facility user ID are managed so as to be associated with each other. For the disease item or the symptom item, a value indicating a disease or a symptom selected and input by the user or a value diagnosed by, for example, the doctor in the hospital is stored. The severity score is a value indicating a degree related to a disease.

The history information item is information for managing the past service usage and abnormal data processing results of the user. For example, the information of the date and time when the user used each service is stored in time series in the history information item. Further, each data item in a case in which practice is performed at that time, that is, data, such as the above-described measurement data, analysis evaluation data, abnormal data detection result, and abnormal data processing content, is stored in the history information item. The information of the address where each data item has been stored may be stored in the history information item.

[Sharing of Abnormal Data Detection Between Local and Server]

In Embodiment 1, the abnormal data detection unit 14 is configured to perform both the non-DB-using abnormal data detection unit 14A and the DB-using abnormal data detection unit 14B. In contrast, in this embodiment, the non-DB-using abnormal data detection unit 14A is performed by the local terminal device 4 of the system 7 and the DB-using abnormal data detection unit 14B is performed by the server 6. The reason for this sharing is that the individual-subject DB 45A and the multiple-subject DB 45B are formed from the data aggregated from a plurality of systems 7 (7A, 7B, . . . ) and the server is suitable for abnormal data detection using the DBs. On the other hand, it is preferable that the local terminal device 4 performs abnormal data detection that does not require the DBs in order to perform the abnormal data detection as soon as possible. Since the local terminal device 4 detects abnormal data, it is possible to detect abnormal data in real time and to immediately issue a re-measurement instruction in a case in which abnormality occurs during measurement. Further, in a case in which the server is not always connected to the network, it is possible to prevent the loss of time required for transmitting data to the server and waiting for the detection results of abnormal data.

The method that shares the abnormal data detection function between the terminal device 4 and the server 6 on the basis of whether or not to use the DB as described above has been described. However, other sharing methods may be used. For example, when many users visit the hospital H1 and a large-scale DB can be constructed, the DB-using abnormal data detection unit 14B may be implemented by the terminal device 4. In addition, in a case in which the authority to collectively change the settings of the abnormality detection reason-processing correspondence table 50B of the management table 50 is given to the administrator of the system, the non-DB-using abnormal data detection unit 14A may also be implemented by the server 6.

[Effects]

According to the abnormal data processing system of Embodiment 3, both the individual-subject DB 45A and the multiple-subject DB 45B are used to achieve highly accurate abnormal data processing, similarly to Embodiment 1. In addition, since the individual-subject DB 45A and the multiple-subject DB 45B are managed by the server, it is considered that data from many facilities can be aggregated to construct a large-scale DB and more accurate abnormal data detection can be achieved. In addition, since the abnormal data detection function is shared between the local terminal device 4 and the server 6, it is possible to detect abnormal data without loss of time.

The invention has been specifically described above on the basis of the embodiments. However, the invention is not limited to the above-described embodiments and various modifications of the invention can be made without departing from the scope and spirit of the invention.

The invention is not limited to the above-described embodiments and includes various modifications. For example, a part of the configuration of one embodiment can be replaced with the configuration of another embodiment and the configuration of one embodiment can be added to the configuration of another embodiment. Further, for a part of the configuration of each embodiment, it is possible to add, delete, or replace the configuration of other embodiments.

INDUSTRIAL APPLICABILITY

It is possible to use an information processing service technique.

REFERENCE SIGNS LIST

1 Abnormal data processing system
2 Measurement system
3 Measurement device
4 Terminal device

The invention claimed is:

1. An abnormal data processing system that acquires a new data including time-series waveform signals from a detector that detects motion information in a finger tapping motion, which is an opening and closing motion of thumb and forefinger of one hand of a subject, and detects whether or not the new data is abnormal and processes the new data, comprising:
   a storage unit that stores an individual-subject database (DB) in which data of an individual subject is accumulated;
   an individual-subject DB divergence degree calculation unit that calculates an individual-subject DB divergence degree which is a degree of divergence of the new data from the individual-subject DB; and
   a calculation unit that calculates the individual-subject DB divergence degree, using a number of data items in the individual-subject DB,
   wherein it is determined whether or not the new data is abnormal on a basis of the degree of divergence, and
   wherein the calculation unit uses an individual-subject DB reliability coefficient which increases as the number of data items in the individual-subject DB increases and weights the individual-subject DB divergence degree with the individual-subject DB reliability coefficient to calculate the degree of divergence.

2. The abnormal data processing system according to claim 1, further comprising:
   an abnormal data processing determination unit that determines a process in a case in which the new data is determined to be abnormal; and an abnormal data processing execution unit that performs the process.

3. The abnormal data processing system according to claim 1, further comprising:

a non-DB-using abnormal data detection unit that determines whether or not the new data is abnormal on a basis of the new data or a feature amount obtained from the new data, without using the individual-subject DB.

4. The abnormal data processing system according to claim 3, wherein the new data is finger movement data, and the non-DB-using abnormal data detection unit uses at least one of a waveform amplitude, a movement non-execution time, and two-hand cooperation calculated from the finger movement data as the feature amount and detects whether or not the feature amount deviates from a predetermined numerical range.

5. An abnormal data processing system that acquires a new data including time-series waveform signals from a detector that detects motion information in a finger tapping motion, which is an opening and closing motion of thumb and forefinger of one hand of a subject, and detects whether or not the new data is abnormal and processes the new data, comprising:

a storage unit that stores an individual-subject database (DB) in which data of an individual subject is accumulated;

an individual-subject DB divergence degree calculation unit that calculates an individual-subject DB divergence degree which is a degree of divergence of the new data from the individual-subject DB; and a calculation unit that calculates the individual-subject DB divergence degree, using a number of data items in the individual-subject DB, wherein it is determined whether or not the new data is abnormal on a basis of the degree of divergence, and wherein the individual-subject DB divergence degree calculation unit has a temporal attenuation divergence degree calculation function that calculates a difference in measurement time between the new data and each data item in the individual-subject DB, calculates past data reliability whose attenuation becomes larger as the difference in measurement time becomes larger, and calculates the individual-subject DB divergence degree from each data item and the past data reliability.

6. The abnormal data processing system according to claim 5, wherein the calculation unit uses an individual-subject DB reliability coefficient which increases as the number of data items in the individual-subject DB increases and weights the individual-subject DB divergence degree with the individual-subject DB reliability coefficient to calculate the degree of divergence.

7. The abnormal data processing system according to claim 5, further comprising:

an abnormal data processing determination unit that determines a process in a case in which the new data is determined to be abnormal; and an abnormal data processing execution unit that performs the process.

8. The abnormal data processing system according to claim 5, further comprising:

a non-DB-using abnormal data detection unit that determines whether or not the new data is abnormal on a basis of the new data or a feature amount obtained from the new data, without using the individual-subject DB.

9. The abnormal data processing system according to claim 8, wherein the new data is finger movement data, and the non-DB using abnormal data detection unit uses at least one of a waveform amplitude, a movement non-execution time, and two-hand cooperation calculated from the finger movement data as the feature amount and detects whether or not the feature amount deviates from a predetermined numerical range.

* * * * *